(12) United States Patent
Matthison-Hansen et al.

(10) Patent No.: US 10,507,126 B2
(45) Date of Patent: Dec. 17, 2019

(54) ENDOSCOPE HAVING A GRASPING TOOL AND A METHOD FOR REMOVING A STENT FROM A PATIENT

(71) Applicant: Coloplast A/S, Humlebaek (DK)

(72) Inventors: Kaspar Matthison-Hansen, Aalsgaarde (DK); Thomas Bachgaard Jensen, Copenhagen (DK); Jakob Bønnelykke Kristensen, Oelstykke (DK); Sebastien Seguy, Gourdon (FR)

(73) Assignee: Coloplast A/S, Humlebaek (DK)

( * ) Notice: Subject to any disclaimer, the term of this patent is extended or adjusted under 35 U.S.C. 154(b) by 303 days.

(21) Appl. No.: 15/162,638

(22) Filed: May 24, 2016

(65) Prior Publication Data

US 2016/0346107 A1    Dec. 1, 2016

(30) Foreign Application Priority Data

May 27, 2015  (EP) ..................... 15305793

(51) Int. Cl.
*A61F 2/95* (2013.01)
*A61B 17/30* (2006.01)

(52) U.S. Cl.
CPC ............. *A61F 2/95* (2013.01); *A61B 17/30* (2013.01); *A61B 2017/305* (2013.01); *A61F 2002/9528* (2013.01)

(58) Field of Classification Search
CPC .. A61F 2/02; A61F 2/82–945; A61F 2/95–97; A61F 2002/047–048; A61F 2002/821–91591; A61F 2002/9505–9665; A61F 2/04; A61F 2/042; A61B 1/012–018; A61B 1/29–295; A61B 2017/2901–2948; A61B 17/29–295; A61M 27/002; A61M 27/008
See application file for complete search history.

(56) References Cited

U.S. PATENT DOCUMENTS

| 4,790,810 A | * | 12/1988 | Pugh, Jr. | ................... | A61F 2/94 604/544 |
| 5,304,183 A | | 4/1994 | Noda | | |
| 5,318,589 A | * | 6/1994 | Lichtman | ............... | A61B 17/29 600/564 |
| 5,499,997 A | * | 3/1996 | Sharpe | ................. | A61B 17/221 606/205 |
| 5,728,121 A | * | 3/1998 | Bimbo | ................... | A61B 17/29 606/207 |

(Continued)

FOREIGN PATENT DOCUMENTS

WO            9600033 A1    1/1996

*Primary Examiner* — Jonathan A Hollm
(74) *Attorney, Agent, or Firm* — Coloplast Corp.; Nick Baumann

(57) ABSTRACT

An endoscope (1) having an operating handle comprising a handle housing (2) and an insertion tube (3) extending from said handle towards a distal end of the endoscope (1) and terminating in a tip part (4) at the distal end of the endoscope (1). The endoscope (1) comprises a tool operating member (22) for operating a tool (55) at the tip part (4). A control means connects the tool operating member (22) and the tool (55), so as to allow movement (55) of the tool in response to activation of said tool operating member (22). Also disclosed is an endoscope including a grasping tool and a method of removing a stent from a patient.

16 Claims, 25 Drawing Sheets

(56) References Cited

U.S. PATENT DOCUMENTS

| | | | | |
|---|---|---|---|---|
| 6,605,036 | B1* | 8/2003 | Wild | A61B 17/29 600/104 |
| 2002/0143387 | A1* | 10/2002 | Soetikno | A61F 2/95 623/1.15 |
| 2003/0069475 | A1* | 4/2003 | Banik | A61B 1/00016 600/152 |
| 2005/0154262 | A1* | 7/2005 | Banik | A61B 1/00059 600/179 |
| 2005/0250983 | A1* | 11/2005 | Tremaglio | A61B 1/0052 600/101 |
| 2005/0277808 | A1* | 12/2005 | Sonnenschein | A61B 1/0008 600/112 |
| 2007/0186933 | A1* | 8/2007 | Domingo | A61B 17/12022 128/207.15 |
| 2007/0276183 | A1* | 11/2007 | Melder | A61B 1/00011 600/112 |
| 2009/0318830 | A1* | 12/2009 | George | A61B 10/0291 600/564 |
| 2010/0234938 | A1* | 9/2010 | Taheri | A61B 17/22031 623/1.23 |
| 2015/0112367 | A1 | 4/2015 | Damarati | |

* cited by examiner

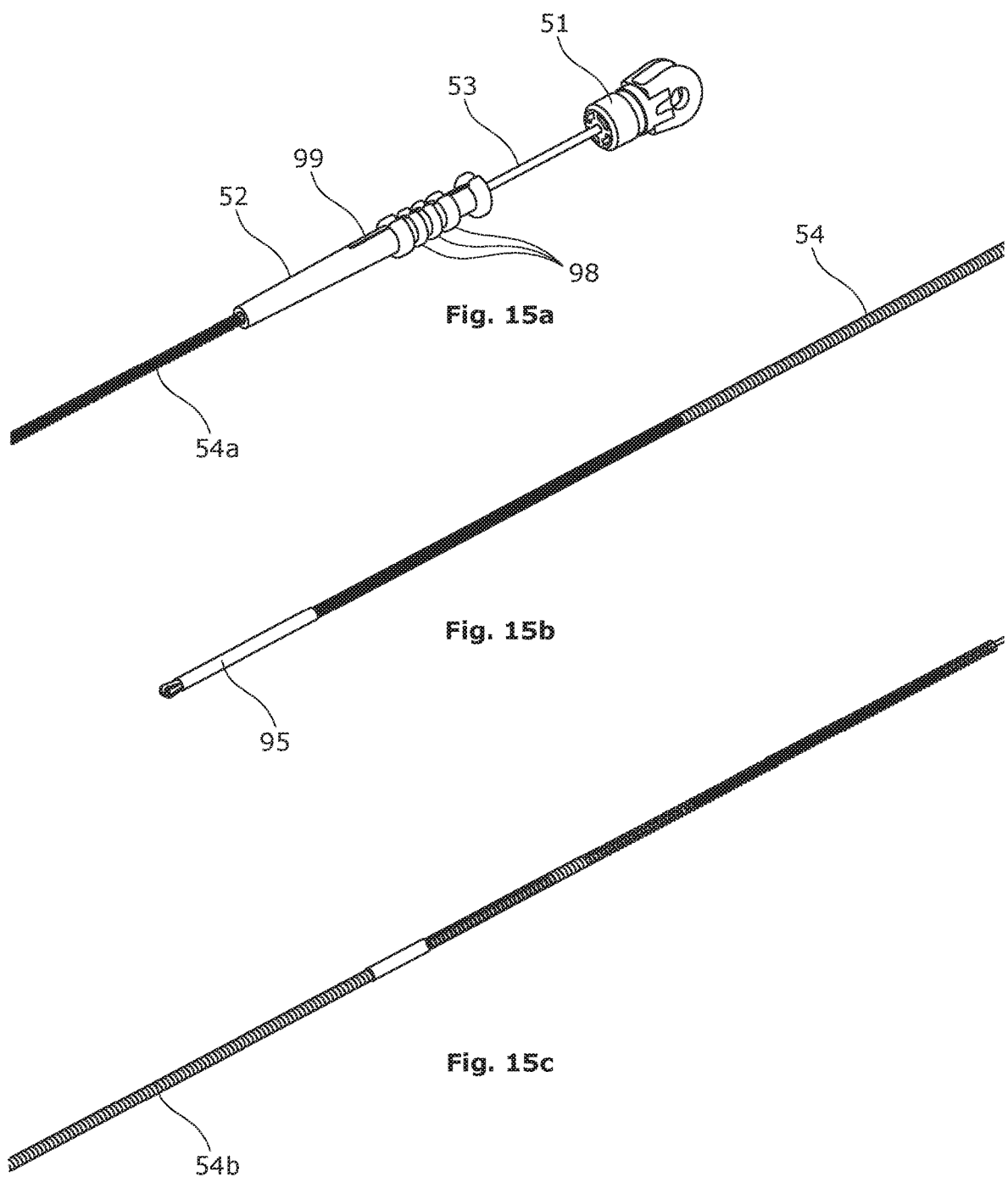

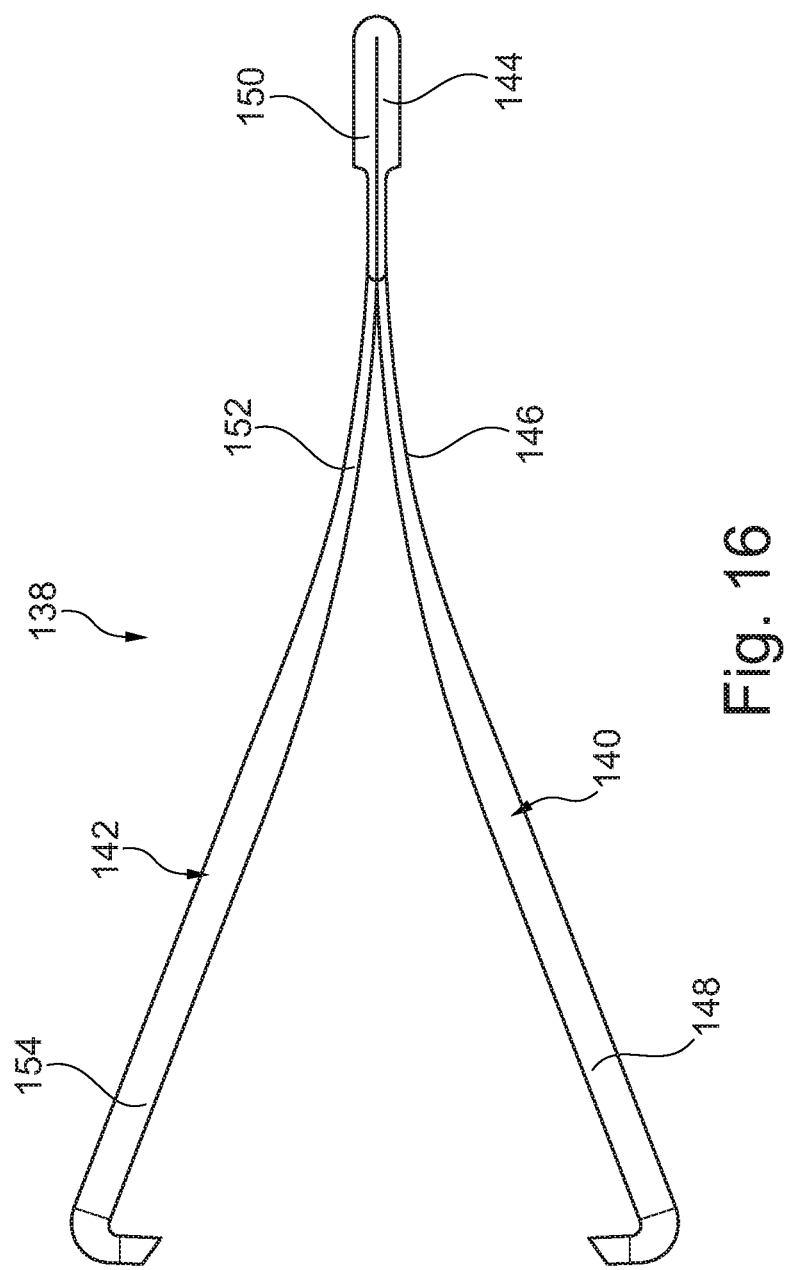

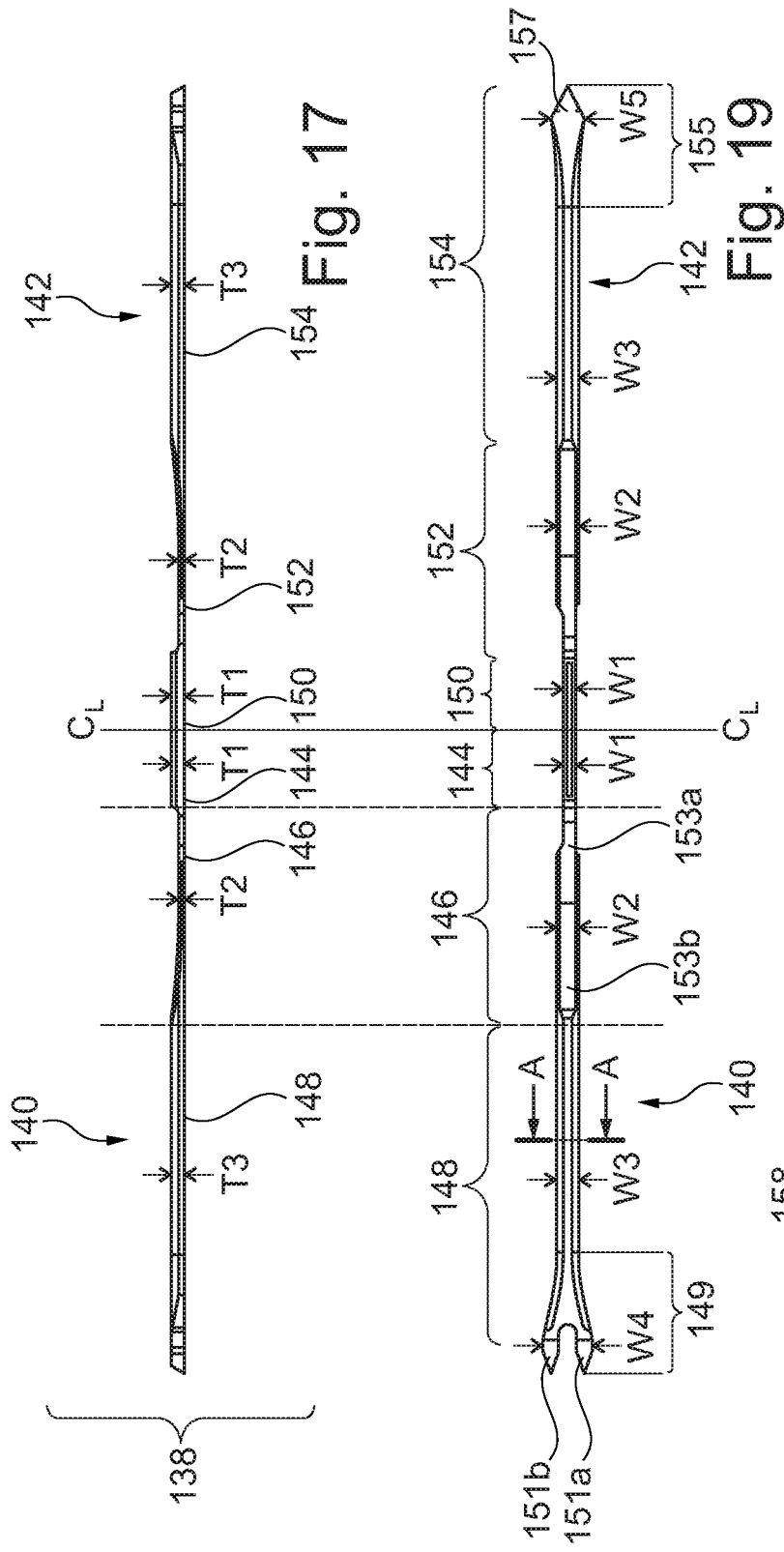

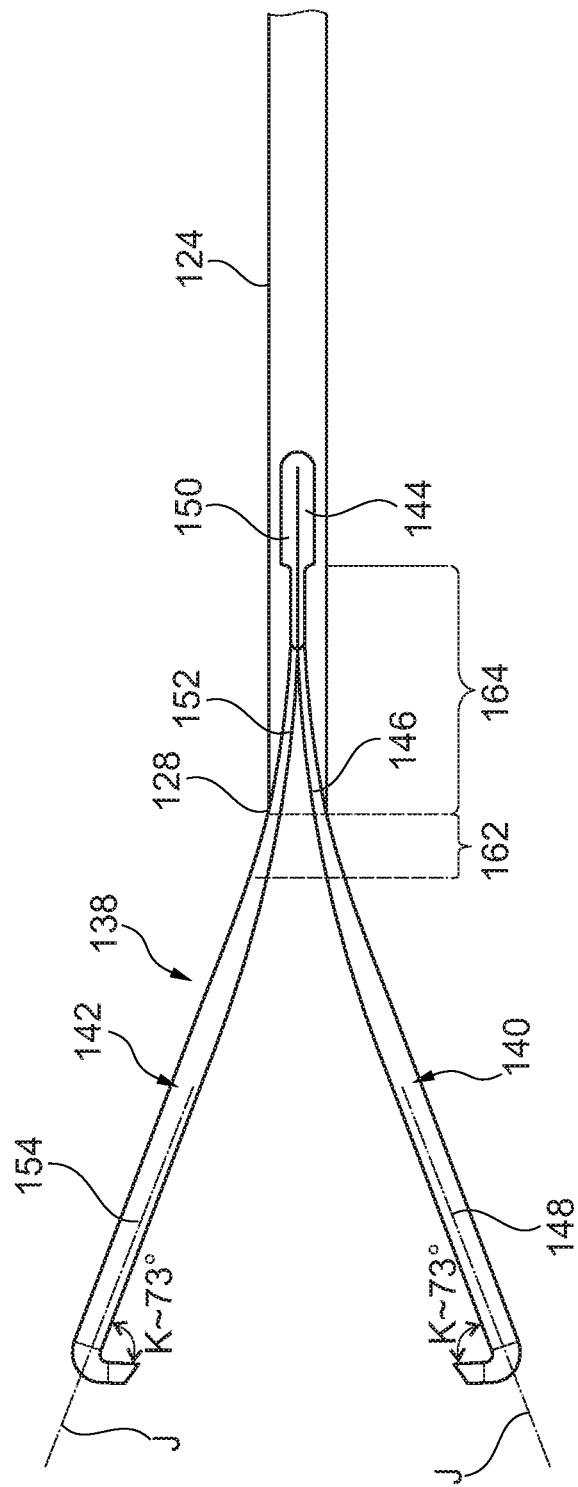

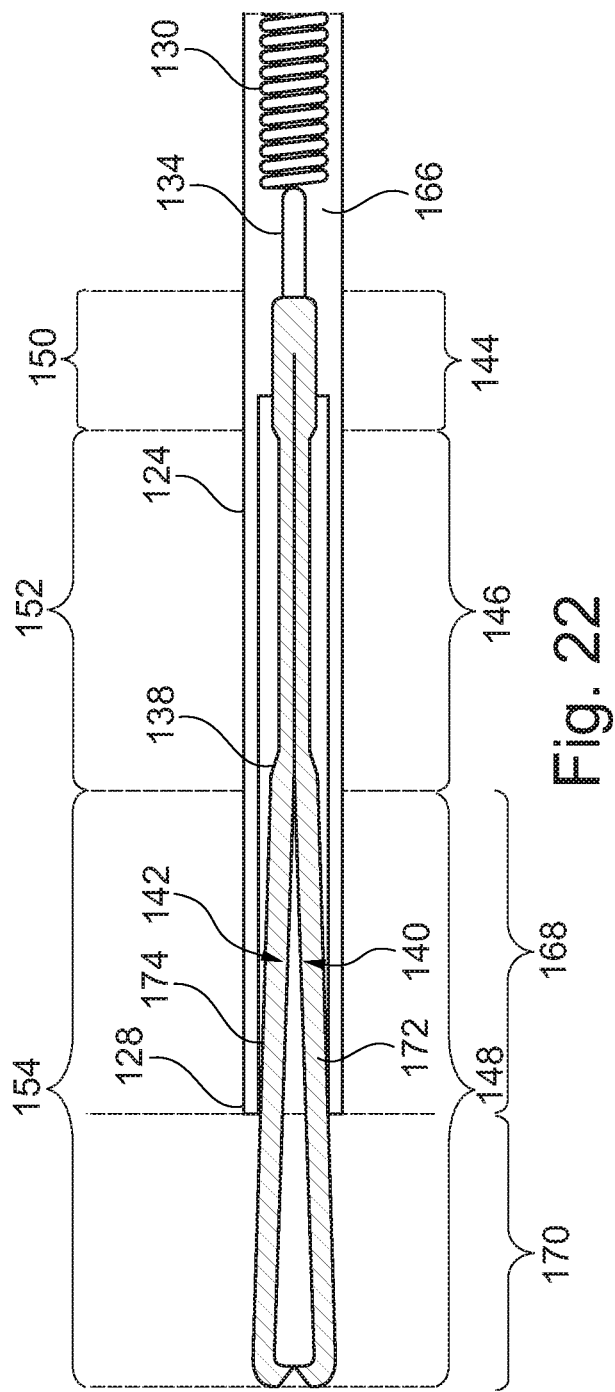
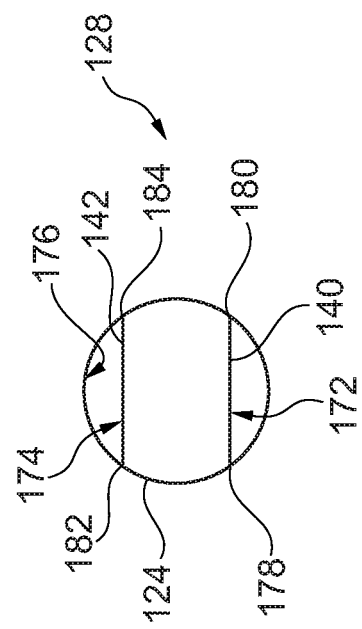

ately a disposable camera endoscope, having an operating handle arranged at a proximal end thereof and an insertion tube extending from said handle towards a distal end of the endoscope.

ENDOSCOPE HAVING A GRASPING TOOL AND A METHOD FOR REMOVING A STENT FROM A PATIENT

The present disclosure relates to an endoscope, in particular but not exclusively a disposable camera endoscope, having an operating handle arranged at a proximal end thereof and an insertion tube extending from said handle towards a distal end of the endoscope.

Most endoscopes comprise an operating handle at the proximal end and an insertion tube extending from the handle towards the distal end. The handle is adapted to be held by an operator and inter alia comprises externally protruding operating members connected to internal control means allowing the operator to control the movement of a bending section at the distal end of the insertion tube, while advancing the distal end of the insertion tube to a desired location e.g. within a body cavity of a person. By means of an attached monitoring device, such as a monitor with a display screen, the location to which the distal end has been advanced may be inspected using the endoscope. Often, however, inspection is not all that is desired, e.g. where the inspection is to locate the site for further actions. One such action could be the removal of a polyp during colonoscopy. Another action could be the removal of an implanted or indwelling stent. Both of which necessitate the use of a tool.

It is an object of the present disclosure to provide an endoscope with an integrated tool capable of performing more complex actions than with currently available solutions.

It is an object of the present disclosure to provide an endoscope allowing the simultaneous control of the more complex actions of the integrated tool as well as the control of a bending section at the distal end of an insertion tube of the endoscope using a single hand only.

It is an object of the present disclosure to provide an endoscope in which the tool is kept stationary during the further action, e.g. while gripping a stent to be removed or closing a loop around a polyp to be removed.

It is an object of the present disclosure to provide an endoscope with an integrated grasping tool that is particularly useful for removing ureteral stents from a ureter of a patient via the patient's bladder and urethra.

It is an object of the present disclosure to provide an endoscope with a grasping tool that is configured to deliver sufficient holding force while requiring minimal, or reduced, operating force.

According to a first aspect of the disclosure these and other objects are achieved by providing an endoscope having an operating handle comprising a handle housing arranged at a proximal end thereof and an insertion tube extending from said handle towards a distal end of the endoscope and terminating in a tip part at the distal end of the endoscope, the endoscope further comprising a tool arranged at said tip part at the distal end of the endoscope, a tool operating member located at the operating handle, a control means connecting said tool operating member and said tool, so as to allow linear movement of the tool in response to activation of said tool operating member, characterized in that said control means is adapted to perform a compound movement of said tool, in response to activation of said tool operating member, said compound movement comprising, in addition to said linear movement of the tool, a task movement, such as opening, closing, gripping, expanding, contracting, pinching, cutting etc.

Thereby it becomes possible to control the tool using the index finger of the operator's hand to perform the complex actions of the tool using the same tool operating member, thus leaving the thumb free for the control of bending section of the insertion tube of the endoscope.

According to one embodiment, said control means is adapted to convert a continuous movement of the tool operating member into a compound movement of the tool in which said a first part of said continuous movement effects the linear movement of the tool, and at least one second part of said continuous movement effects the task movement of the tool. Thereby it furthermore becomes possible to perform the linear advance of the tool and carry out task movement of the complex action in one single movement of the tool operating member.

According to one embodiment, the control means, or control element, comprises a rotary member rotatable in response to operation of said tool operating member, a first lever rigidly connected to said rotary member at one end, a second lever rigidly connected to said rotary member at one end, where the first and second levers, respectively, have a length selected to provide different motion patterns of a first motion transfer member and a second motion transfer member effecting in conjunction said compound movement of the tool. Thereby it becomes possible to adapt the control of the task movement with respect to the linear movement in accordance with the specific needs for a specific tool.

According to one embodiment, said rotary member is a pinion and said control means or element comprises a rack in engagement with said pinion and connected to the tool operating member. This is a simple and reliable mechanical solution, which may readily be accommodated in the handle housing of the endoscope, preferably by means of an internal chassis.

According to one embodiment, the endoscope comprises a first motion transfer member having a first end in articulated connection with a second end of said first lever, the second end of the first motion transfer member being connected to the tool, a first arm in articulated connection with said second lever at one end and at a second end in articulated connection with a first end of a second motion transfer member, where the first and second levers, respectively, have a length selected to different motion patterns of the first and second motion transfer members in response to one and the same activation movement of the tool operating member. Thereby it becomes further possible to achieve a desired complex activation for a specific requirement of the tool, using still a single movement of the tool operating member.

According to one embodiment, the first motion transfer member comprises a wire and that the second motion transfer member comprises a sheath surrounding said first motion transfer member. Thereby a reliable mechanical solution, where the sheath protects and supports the wire is obtained.

According to one embodiment, said second motion transfer member comprises two or more sectors differing from each other in rigidity. Thereby the motion transfer members become adapted to differing rigidities of the insertion tube, thus not adversely affecting the flexibility of the of the insertion tube.

According to one embodiment, said second end of said second motion transfer member comprises a rigid tube sector. Thereby good control of the linear movement of the tool outside of insertion tube during operation is achieved.

According to one embodiment, said pinion is non-circular. Thereby it becomes further possible to adapt the control of the task movement with respect to the linear movement in accordance with the specific needs for a specific tool. At the same time, it becomes possible to influence the necessary force required by the index finger on the tool operating member of the endoscope.

For similar reasons said rack in one embodiment is curved. This in turn also allows optimisation of the way the space within the handle housing is utilized.

In one embodiment, the endoscope comprises a chassis adapted to support said pinion. Thereby the assembly of the endoscope is facilitated as the housing need not carry movable parts.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. Some figures are side views of a tubular component such as a sheath or insertion tube for which views it is to be understood that a portion facing the observer is removed for illustration purposes. The elements of the drawings are not necessarily to scale relative to each other.

FIGS. 15A-C show different sectors of motion transfer means comprising a first motion transfer member and a second motion transfer member.

FIG. 16 is an enlarged side view of one embodiment of a grasping head of a grasping tool.

FIG. 17 is a side view of one embodiment of a grasping head.

FIG. 19 is a top view of one embodiment of the grasping head of FIG. 17.

FIG. 19A is a cross section taken along the line A-A in FIG. 19.

FIG. 21 is a side view of one embodiment of a grasping head.

FIG. 22 is a side view of one embodiment of a grasping head.

FIG. 22A is an enlarged end view of one embodiment of the grasping tool.

DETAILED DESCRIPTION

Figure 2:
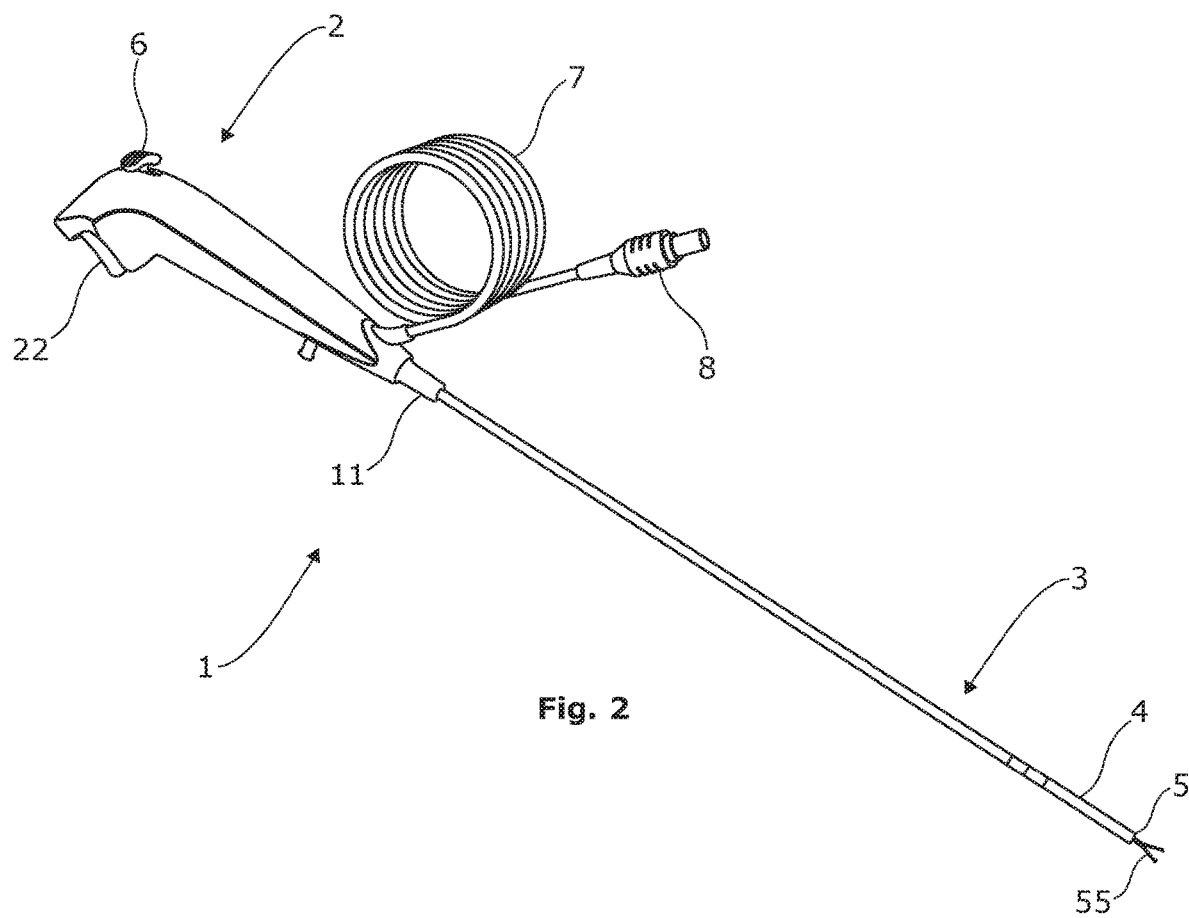
FIG. 2 shows a perspective view of the endoscope of FIG. 1 in assembled state.
Figure 4A:
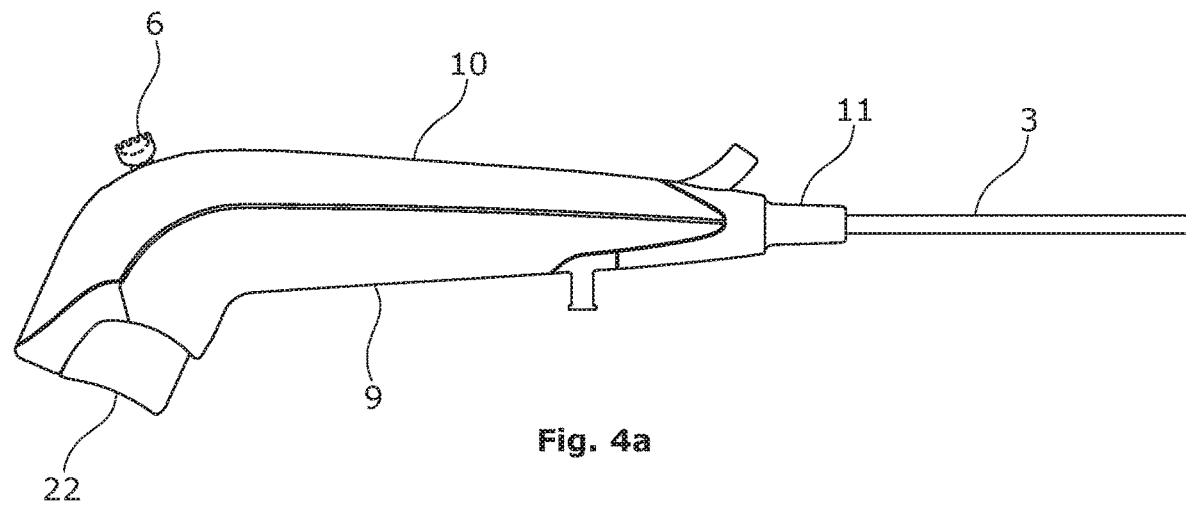
FIG. 4A and FIG. 4B show partial views of the endoscope of FIG. 1 with the tool operating member in released and depressed state, respectively.
Figure 4B:
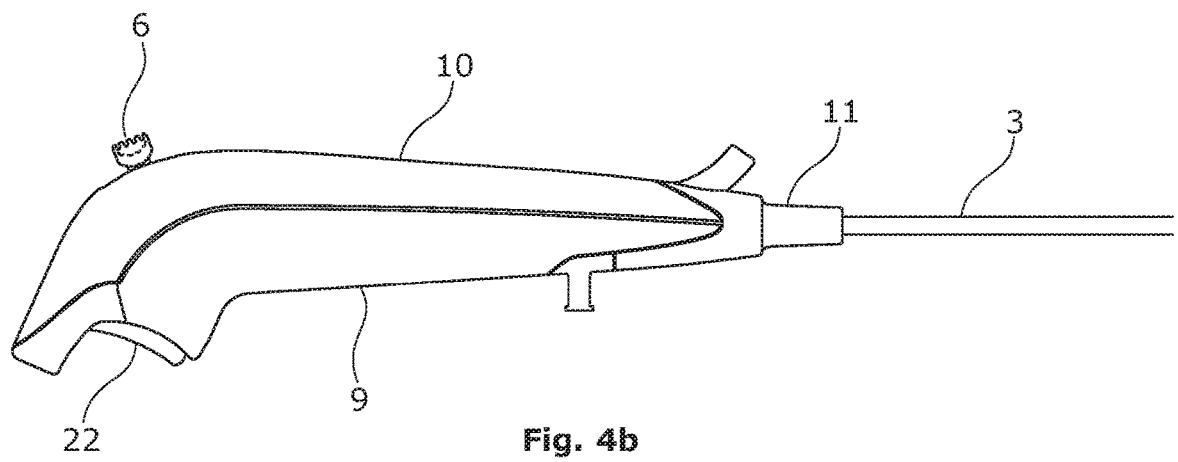

Turning first to FIG. 2, one embodiment of an assembled endoscope 1 according to the present disclosure is shown. The endoscope 1 has a proximal end with an operating handle 2 to be held in one hand by an operator. Accordingly, the operating handle is shaped in a manner ergonomically suitable for operator, in particular but not exclusively for the hand of the operator, as arms and joints may also play a role in the ergonomics. From the handle 2, an insertion tube 3 extends towards the distal end of the endoscope. At the distal end of the endoscope 1, the insertion tube 3 ends in a bending section 4 and a tip part 5. The bending section 4 is in mechanical connection with a first operating member 6, digitally operable by the operator, e.g. by the thumb, thereby allowing the operator to bend the tip part 5 in a desired direction when advancing the insertion tube 3 towards a desired location, e.g. through a body cavity of a patient. In addition to the first operating member 6 the endoscope 1 comprises a tool operating member 22 adapted to operate a tool 55 at the tip part 5 of the endoscope 1 handle comprises. The tool operating member 22 is preferably in the form of a trigger or push-button so accommodated in the housing that it may be operated by the same hand as used for operating first operating member 6. In the configuration shown the first operating member 6 is adapted to be operated by the thumb of the operator whereas the push-button is adapted to be depressed independently thereof by the index finger of the very same hand of the operator. This allows singled handed use of the endoscope. As can be seen the push-button is has been partially depressed allowing the tool 55 to be advanced forwardly from the distal end of the tip 5 of the endoscope 1. This partially depressed position, which will be described in greater detail later, is an intermediate position between the fully released position shown in FIG. 4A, towards which the push-button is preferably spring biased, and the fully depressed position shown in FIG. 4B, which will also be described later. As the endoscope and tool allows single handed use of the endoscope, methods of operation can be obtained in which a single health care professional can operate the endoscope and tool, thereby reducing the number of staff required to carry out a procedure, in turn providing easier access to the procedure and reduce the costs involved.

Figure 3:
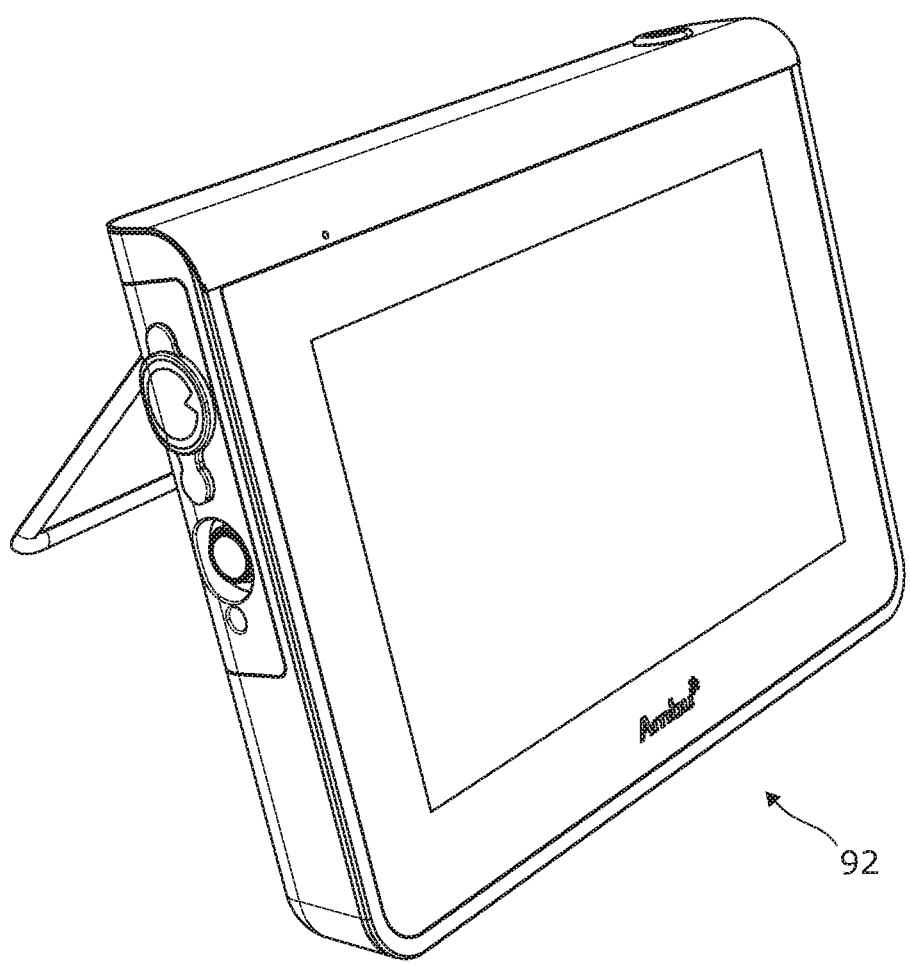
FIG. 3 shows a monitoring device for mutual connection with the endoscope of FIG. 1.

As can also be seen in FIG. 2, the endoscope 1 comprises a flexible connection cable 7 with a connector 8 allowing the endoscope 1 to be connected to a monitoring device such as a monitor 92 shown in FIG. 3 forming part of an endoscope 1 and monitor 92 system.

Figure 1:
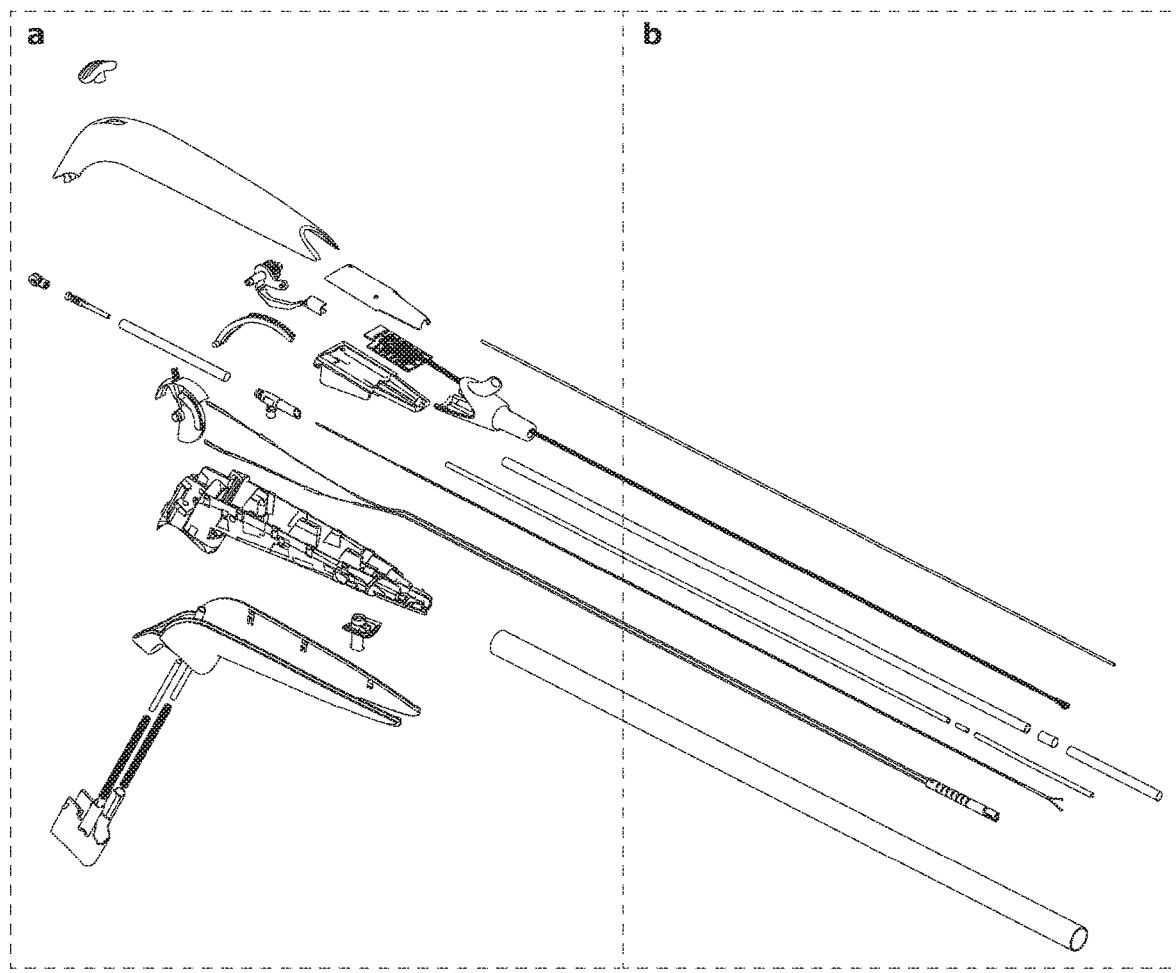
FIG. 1 shows an exploded overview of one embodiment of an endoscope including a tool according to the present disclosure indicating view halves "a" and "b", corresponding to FIGS. 1A and 1B respectively.
Figure 1A:
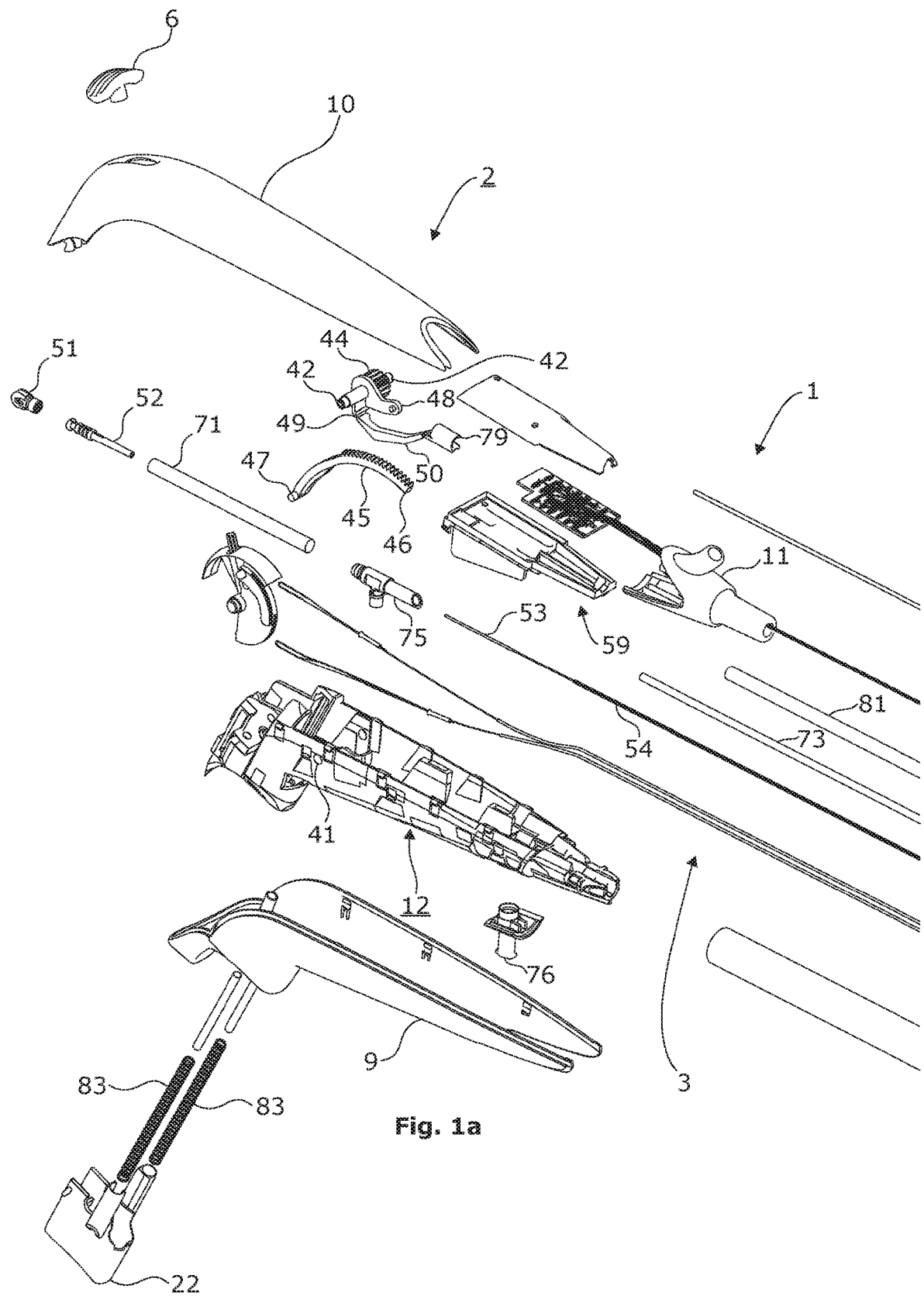
FIG. 1A corresponds to half side "a" of the view of FIG. 1 and shows an exploded view of a first portion of one embodiment of an endoscope including a tool according to the present disclosure.
Figure 1B:
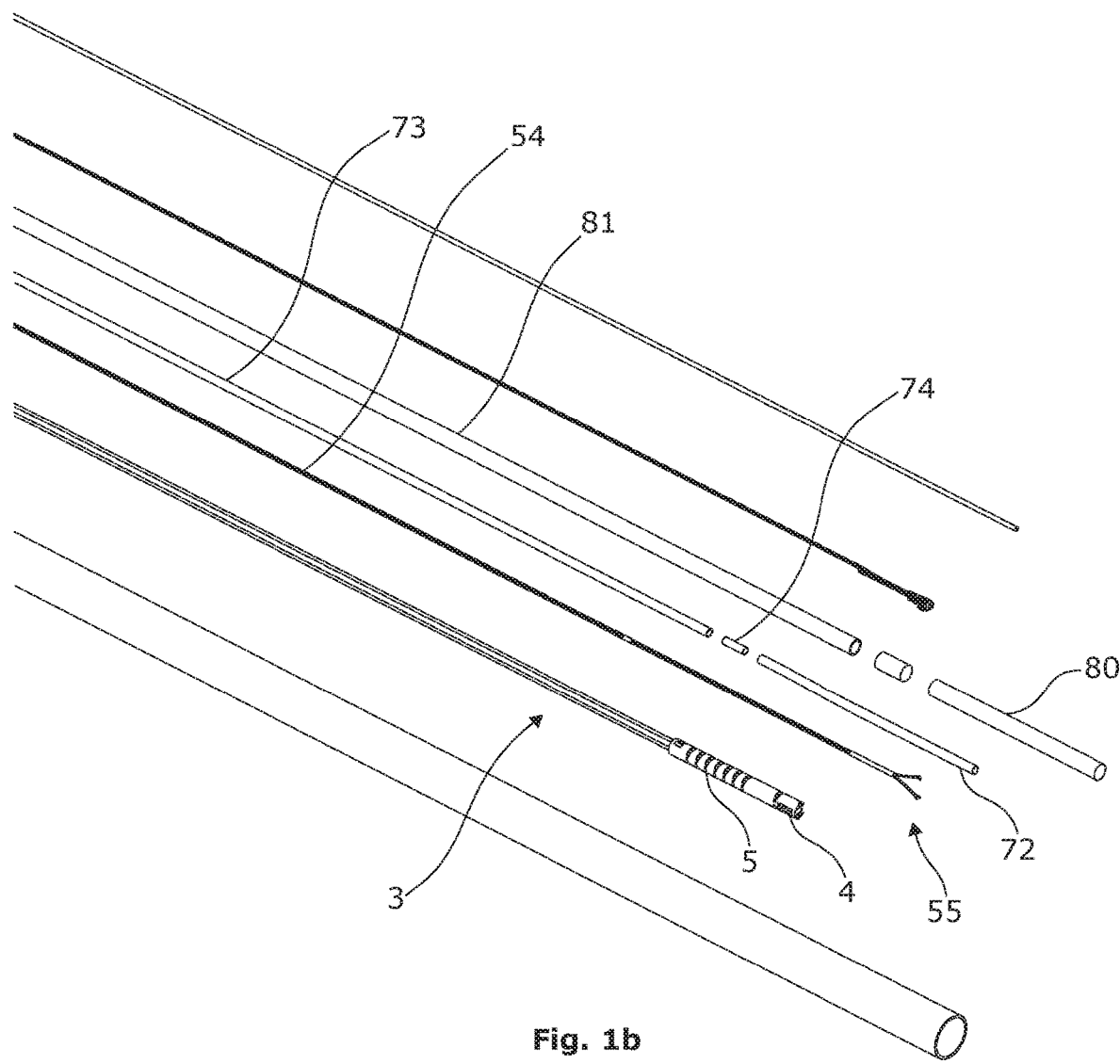
FIG. 1B corresponds to half side "b" of the view of FIG. 1 and shows an exploded view of a second portion of one embodiment of an endoscope including a tool according to the present disclosure.

Turning now to FIG. 1 an exploded view of the endoscope 1 is shown. As mentioned, the endoscope 1 has an operating handle 2 at the proximal end thereof i.e. at the left-hand side of FIG. 1. The operating handle 2 is assembled from and comprises a number of handle parts to be described later. From the operating handle 1, the insertion tube 3 comprising a number of insertion tube parts to be described later extends towards the distal end of the endoscope, i.e. towards the right-hand side of FIG. 1.

The operating handle 2 comprises at least two shell parts 9, 10 forming the outer housing walls of the handle housing of the operating handle 2. The two shell parts 9, 10 form the outer housing walls and are shaped to provide an ergonomically suitable operating handle for an operator, gripping it with one hand. In addition to the two shell parts 9, 10 a transition part 11 forming the transition from the operating handle to the insertion tube 3, may be provided. This transition part may also form part of the handle housing. However, the two shell parts 9, 10 constitute the major part of the housing in the embodiment shown. The shell parts 9, 10 and almost all other parts are mounted on a chassis 12.

Figure 5:
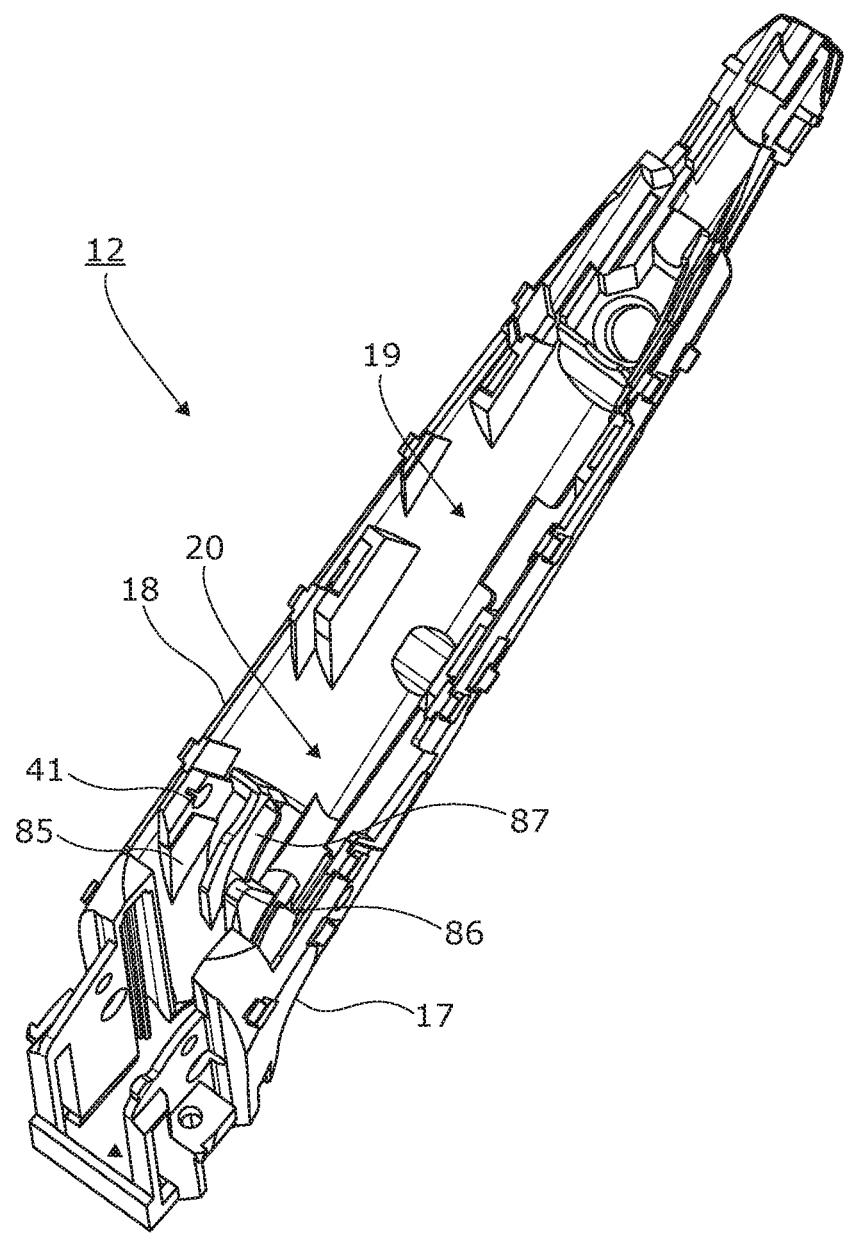
FIG. 5 shows show an internal chassis of the endoscope.
Figure 6:
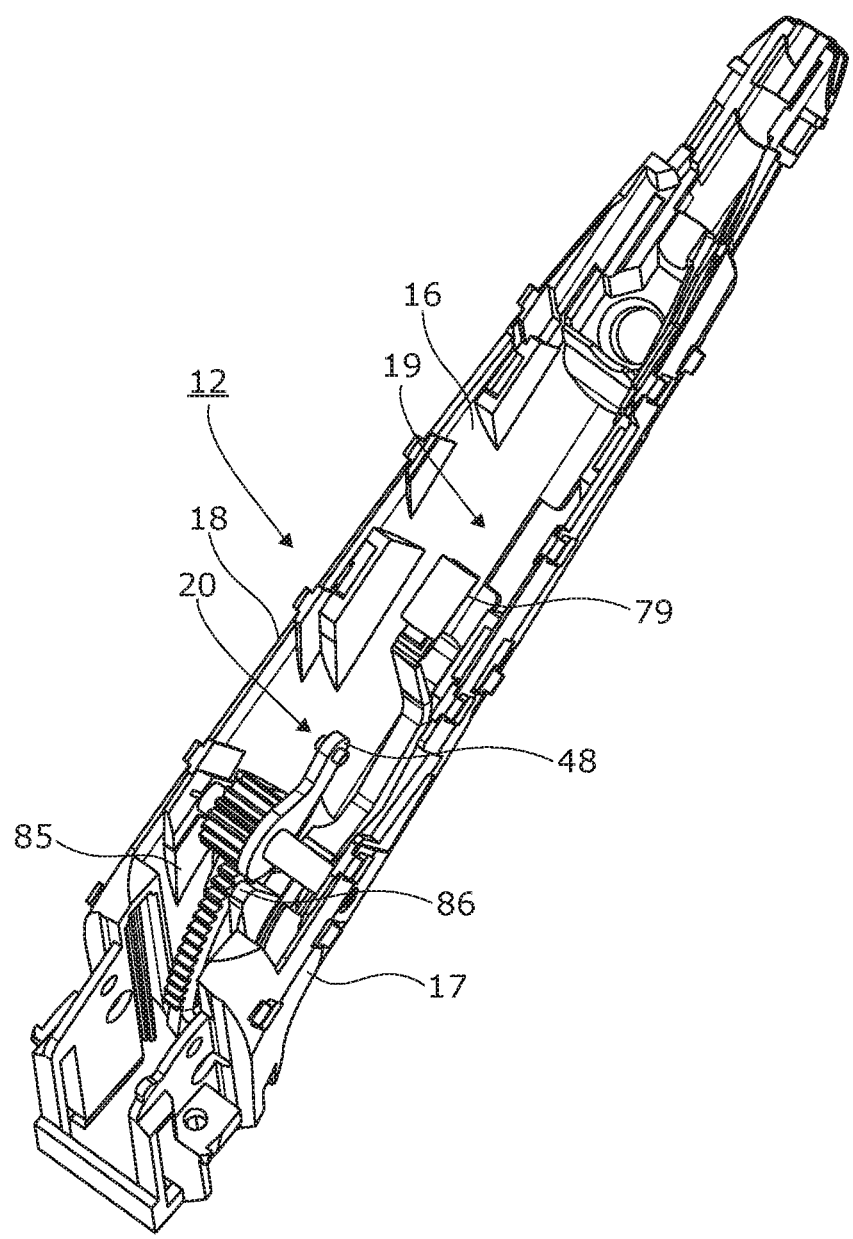
FIG. 6 shows the chassis of FIG. 5 with a rack and pinion mounted.
Figure 7:
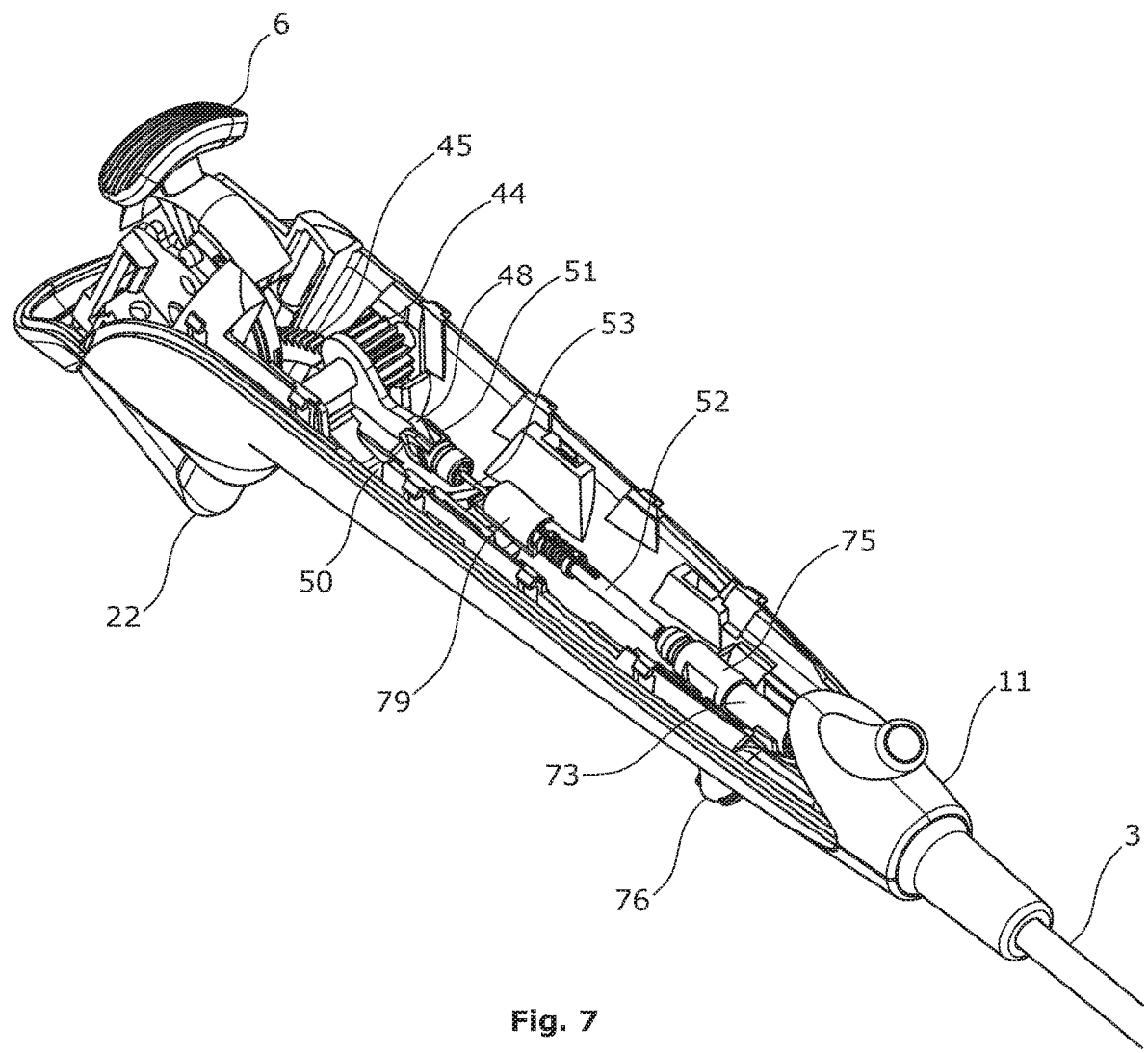
FIG. 7 shows the chassis of FIG. 6 partially mounted in the handle housing partially mounted in the handle housing and with rack and pinion of FIG. 6 attached to a motion transfer means.
Figure 8:
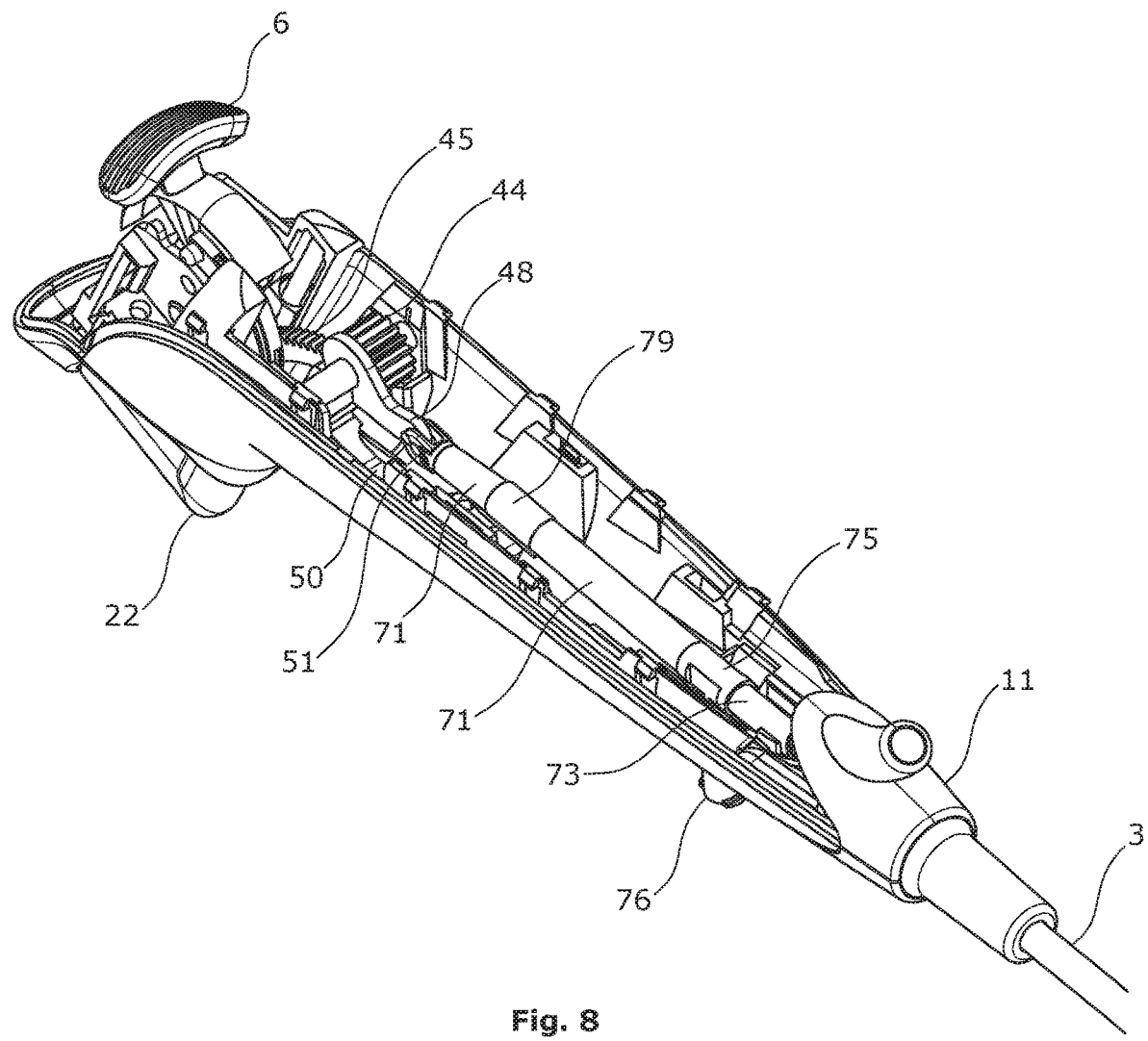
FIG. 8 is similar to FIG. 7, but with the motion transfer means enclosed in a part of the working channel of the endoscope.

As best seen in FIG. 5, the chassis 12 preferably shell shaped, i.e. the chassis 12 comprises an essentially shell shaped structure with a shell wall having an inner surface 16 and an outer surface 17 linked by an edge 18, said essentially shell shaped structure defining an interior compartment 19 delimited by said inner surface 16 and the edge 18 of the shell wall, the edge thus defining main opening 20 of said interior compartment 19. It will be understood that the chassis 12 can be designed mainly based on technical requirements, in such as kinematic chains of movable parts to be described further below, and thus be optimized for those technical requirements without having to inherit constraints from the ergonomic requirements of the handle 2, i.e. the shape of the two shell parts 9, 10.

As mentioned above, the chassis 12 is adapted to for the mounting of almost all parts of the endoscope 1. In particular, the chassis 12 is adapted for holding movable parts forming of kinematic chain from the push-button forming the tool operating member to the motion transfer means transferring the movement of the tool operating member 22 to the tool 55.

Figure 9:
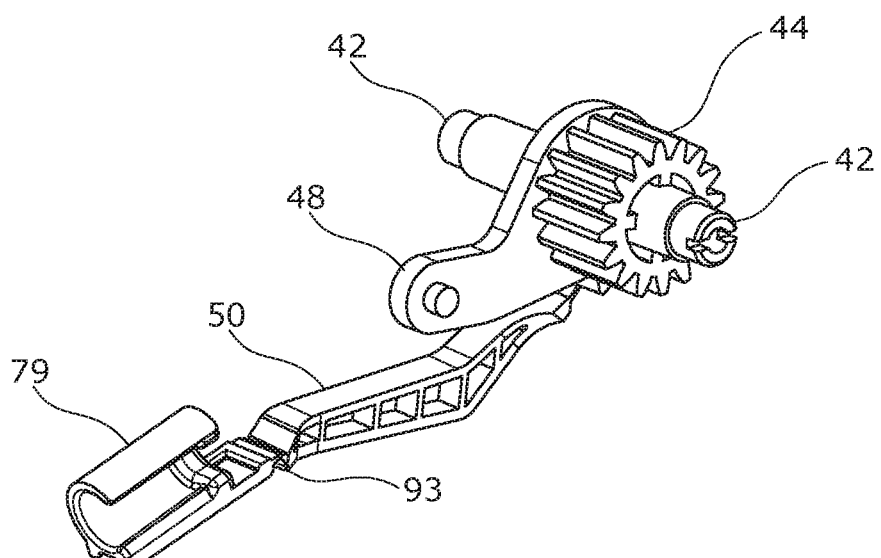
FIG. 9 shows a first perspective view of the pinion of FIG. 6.
Figure 10:
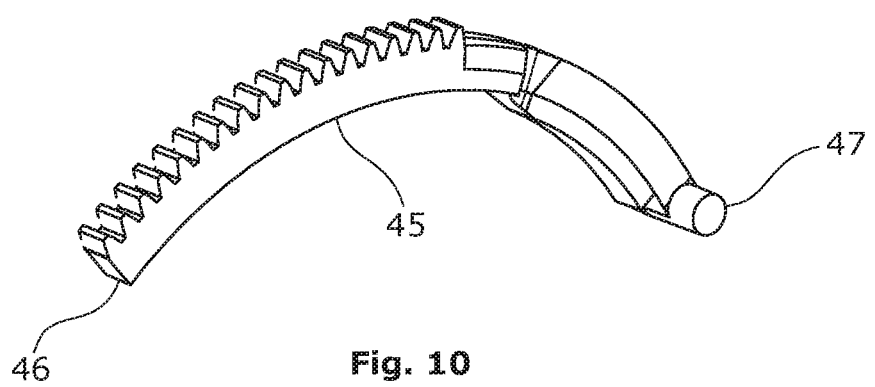
FIG. 10 shows a perspective view of the rack of FIG. 6.
Figure 11:
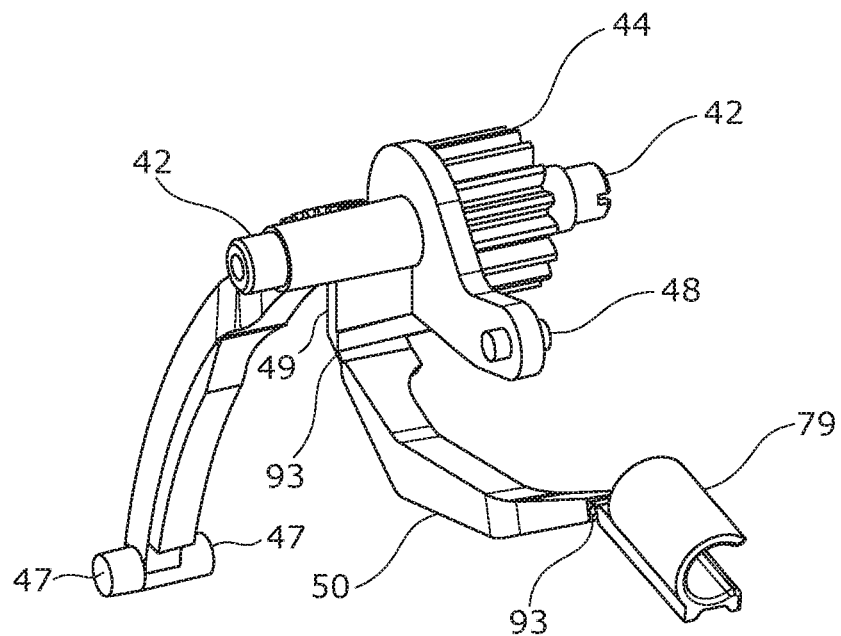
FIG. 11 shows a second perspective view of the pinion of FIG. 6.
Figure 13:
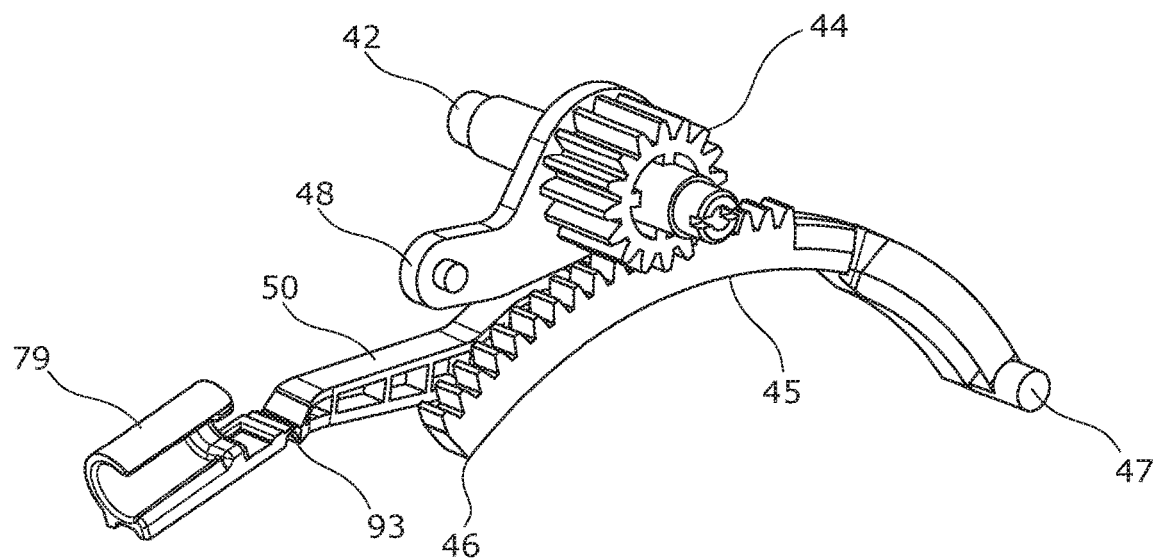
FIG. 13 shows a second perspective view of the rack and pinion of FIG. 6 in mutual engagement.
Figure 14:
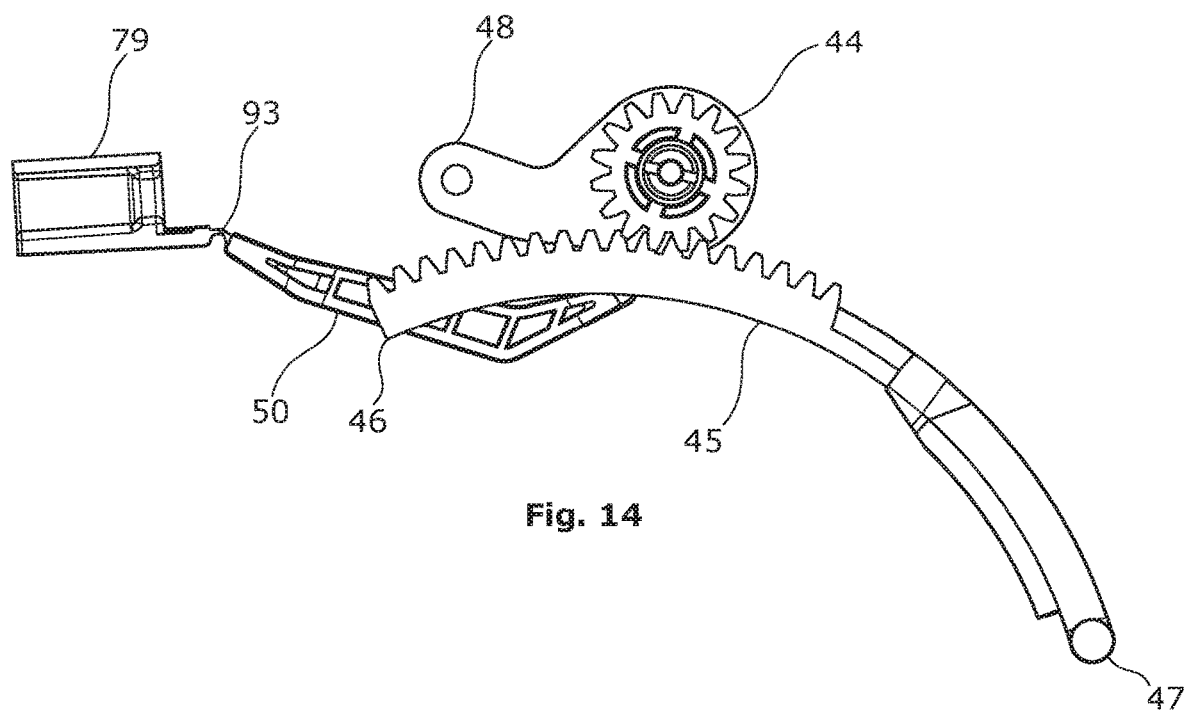
FIG. 14 shows a plan view of the rack and pinion of FIG. 6 in mutual engagement.

One such adaptation is a pair of apertures 41 in the form of essentially cylindrical through holes can be seen in FIG. 1. The apertures 41 serve as bearings of trunnions 42 carrying rotary member such as a pinion 44, best visible in FIG. 9. As can be seen from FIGS. 12 to 14, the pinion 44 is adapted to be in engagement with a curved rack 45. The curved rack 45 is shown separately in FIG. 10. The curved rack 45 has a first free end 46 and a second end with trunnions 47 held loosely in suitable receptacles inside the push button forming the tool operating member 22. The rack 45 as such is loosely held in a guideway comprising a first side 85, a second side 86 and a curved bottom 87 adapted to keep the rack 45 in engagement with the pinion 44. The first side 85 and the second side 86 as well as the curved bottom 87 are preferably formed integrally with the remainder of the chassis 12, e.g. in an injection moulding process. The first side is preferably constituted by a plane surface of a thickened part of the wall, i.e. a raised part of the inner surface 16 of the chassis 12.

Rotation of the pinion 44 may be effected by an operator moving the push-button forming the tool operating member 22, e.g. depressing it using an index finger, upon which the push-button forming the tool operating member 22 transfer motion to the curved rack 45, in turn rotating the pinion 44.

On the pinion 44, two levers 48 and 49 are provided. These levers 48 and 49 are in rigid connection with the pinion 44. The levers 48 and 49 have different lengths so as to influence a first motion transfer member 53 and a second transfer member 54 of the motion transfer means in different ways in order to effect a compound movement of the tool 55. As will be described later this compound movement comprises both a linear movement of the tool 55 and a task movement of the tool 55.

As can best be seen in FIG. 1, the first motion transfer member 53 is arranged co-axially within the second motion transfer member 54. The first motion transfer member 53 and the second motion transfer member 54, in turn, are arranged within in tubular members 71, 72, 73, 74, which form part of the working channel of the endoscope, together with an e.g. T- or Y-shaped bifurcated section 75 providing the entry port to the working channel.

As can best be seen from FIGS. 15A-15C the first and second motion transfer members 53, 54 each comprise different sectors with different rigidities or bending properties, matching the requirements of the insertion tube 3, and the working channel, which both also has different bending properties along the length thereof. The first motion transfer member 53 preferably comprises a rigid rod piece at the proximal end and a rod or tubular piece at the tool 55. Between the two, the first motion transfer means may comprise s flexible wire.

The first motion transfer member 53 is terminated in an end sealing means 51. The first motion transfer member 53 is terminated in an end sealing means 51. Apart from sealing the proximal end of the working channel, the end sealing means also serves as part a first kinematic chain by being pivotally connected to the first lever 48.

The first kinematic chain is as follows: Depressing the tool operating member 22 will move the rack 45 in a curvilinear movement via the trunnions 47. The rack 45, which has teeth in engagement with the pinion 44, will rotate the pinion 44 and the first lever 48 rigidly connected thereto. The rotating first lever will consequently push the proximal end of the first motion transfer member 53, causing the tool 55 arranged at distal end of the first motion transfer member 31 to be moved out of the working channel beyond the distal end of the insertion tube 3 of the endoscope 1. Being spring biased, by e.g. a pair coil springs 83 accommodated in the chassis 12, a release of the tool operating member 22 will automatically return the tool operating member 22 to the position of FIG. 4A The second motion transfer member 54 forms a sheath for the first motion transfer member and preferably comprises a coil spring part 54a wound from wire with a rectangular cross section towards the proximal end, and a coil spring part 54b wound from wire with a circular or round cross section towards the distal end. At the distal end, the second motion transfer member is terminated in a rigid tubular member 95.

The second motion transfer member 54 is terminated in a first tubular end member 52. The rigid part of the first motion transfer member 53 passes co-axially through the first tubular end member 52 and into the remainder of the second motion transfer member 54. The passage through the first tubular end member 52 as well as through the remainder of the second motion transfer member 54 is adapted to allow mutual lengthwise relative motion, i.e. mutually reciprocating movement.

Figure 12:
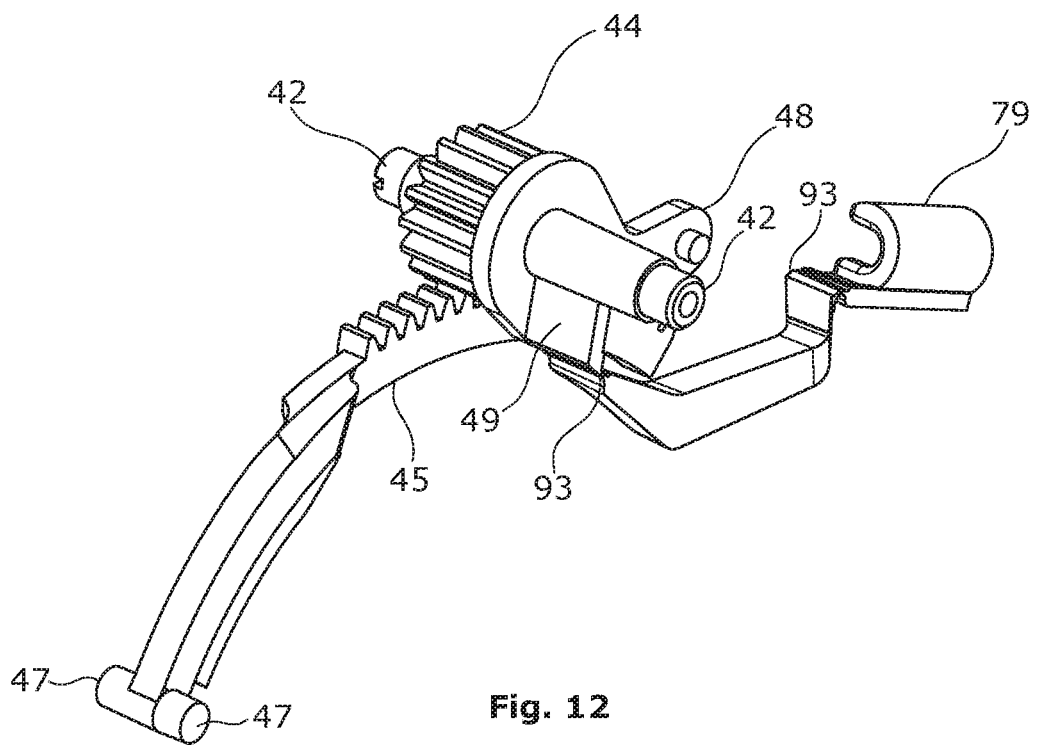
FIG. 12 shows a first perspective view of the rack and pinion of FIG. 6 in mutual engagement.

Not unlike the sealing end member 51, the first tubular end member 52 serves as part of a second kinematic chain adapted to provide a different motion pattern of the second motion transfer member 54 as compared to the first motion transfer member 53 in response to the very same depression, i.e. one and the same as the one described above. This is achieved by the second lever 49, which is also rigidly attached to the pinion 44 but has a different length than the first lever 48. At the end of the second lever 49, a first arm 50 is provided in articulated connection with said second lever 49. The second end of the first arm 50 is in articulated connection with a clamping means 79 adapted to clamp the tubular end means 52 with a part 71 of the working channel wall interposed. The interposed part 71 is preferably a flexible hose part. Preferably, the flexible hose part is made from the very same tubular material as is used to form the outer sheath 80 of the insertion tube 3 at the distal end around the bending portion 5. To ensure good grip between the interposed part of the working channel wall 71 and the first tubular end member 52 the first tubular end member may comprise concentric ribs 98 or corrugations, or similar means. The articulations of the first arm 50 are preferably provided as integrally moulded foil hinges 93, as best seen in FIG. 12.

Accordingly, the second kinematic chain is as follows: Depressing the operating member 22 will move the rack 45 in a curvilinear movement via the tool trunnions 47. The rack 45, which has teeth in engagement with the pinion 44, will rotate the pinion 44 and the second lever 49 rigidly connected thereto. The rotating second lever 49 will consequently push the proximal end of the first arm 50, thereby moving clamping means 79 at distal end of the first arm 50, articulating the first arm 50 as necessary in the foil hinges 93. The clamping means 79 moves the clamped part of the working channel wall part 71. Being clamped, the clamped part of the working channel wall 71 moves the first tubular end member of the second motion transfer member 54 towards the distal end of the working channel, consequently causing the distal end of the second motion transfer member 54 to be moved out of the working channel beyond the distal end of the insertion tube 3 of the endoscope 1. The distal end of the second motion transfer member 54 is preferably terminated in a second tubular end member 95. Being spring biased, by e.g. a pair coil springs 83 accommodated in the chassis 12, a release of the tool operating member 22 will automatically return the tool operating member 22 to the position of FIG. 4A.

Providing these two different kinematic chains allows the tool 55 to perform a compound movement comprising both a linear movement and a task movement, during one continuous depression of the tool operating member 22. In the linear movement, the tool 55 is advanced to a position in front of the distal end of the insertion tube 3 of endoscope 1 where it is visible from the camera built into the tip part 4 of the endoscope 1, and hence visible by the operator on the monitor 92 attached to the endoscope via cable 7 and connector. This may be performed by only partially depressing the tool operating member 22, e.g. to the position shown in FIG. 2, where with a suitable layout of the first kinematic chain will not advance any further but remain stationary or at least almost stationary with respect to the distal end of the insertion tube 3 of the endoscope even if the tool operating member is depressed further. Having located the correct position for operating the tool 55, e.g. by laterally moving the tip 4 of the bending section 5 at the distal end of the insertion tube 3 of the endoscope 1 using the first operating member 6 simultaneously with the tool operating member, the task movement can be performed.

In one embodiment the tool 55 at the distal end of the first motion transfer member 53 comprises a grasping head having self-expanding configuration, such as a pair of spring tweezers, jaws, forceps, a spring loop, or the like which, when it is accommodated in the tubular member 95 is compressed, as shown in FIG. 15B. Accordingly, it will auto-expand if it is advanced out the second tubular member 95, to the configuration shown in FIG. 2. Embodiments of a tool comprising a grasping head will be described in further detail below. Due to the second kinematic chain operating independently of the first kinematic chain, the second motion transfer member is held stationary is in the working channel during the first part of the depression of the tool operating means 22 to the intermediate position. Then, still due to the independent operation of the first and second kinematic chains, continuing the continuous movement by further depressing of the tool operating member 22 will cause the second motion transfer member to start moving thereby advancing the second tubular end member 95. Consequently, the second tubular end member 95 slides over the tool 55 again, because as mentioned above the first kinematic chain is laid out to keep the tool 55 stationary in the field of vision of the camera at a distance from the tip part 4 of the insertion tube 3 of the endoscope 1. This will the effect the task movement of closing the tool 55 because the configuration as show in FIG. 15B is now restored, but this time at the position at the location outside the working channel set at the intermediate depression of the tool operating member 22. Keeping this position is of outmost benefit for the operator, who having only one camera eye does not perspective vision and therefore as difficulties in judging distances. Thus, having found the position where a stent a polyp or other object is to be gripped, e.g. by touching them with the tool, he can do so without further advancing or retracting of the entire endoscope 1.

Having gripped an object, such as a stent, with the tool 55 in this way the object may then be removed from the body by retracting the entire endoscope 1 from the cavity whilst holding the tool operating member 22 depressed.

For the sake of clarity, it should be noted that the term continuous movement is merely to be understood as a movement of the tool operating member from released state to a depressed state. It does not imply that the movement cannot be paused by the operator during the continuous movement. It does also not imply that the movement cannot be reversed partially reversed by the operator releasing the tool operating member 22, in the search for the gripping location.

As mentioned above, and as can be seen from FIGS. 10 and 12-14 the rack 45 has a curvature. This curvature preferably matches the curvature of the curved bottom 87 of the guideway, so that the teeth of the rack 45 are kept in engagement with the matching teeth of the pinion 44. This curvature saves space helping to fit the rack 45 and pinion 44 mechanism within the chassis 12 and the handle housing 2. The skilled person will understand that the forces and torques of the kinematic chain may be also be influenced by suitable choice of curvature and length of the rack 45 and diameter of the pinion 44 provided it is generally circular. The pinion 44 with a generally oval shape or other curvature is also envisaged. The skilled person will also understand that the two kinematic chains, and in particular their mutual differences could be influenced by suitable choice of the length of the levers 48 and 49, their angular spacing on the pinion 44, and the length and articulations of the arm 50, as well as by the provision of further arms. This may allow specific adaptation of the kinematic chains to the specific requirements of different tools 55.

As will be understood from the above the first and second motion transfer members are located within the working channel of the endoscope 1, comprising tubular members 71, 72, 73, 74 forming a generally tubular working channel wall and an e.g. T- or Y-shaped bifurcated section 75 providing the entry port to the working channel.

Starting from the proximal end of the endoscope 1, a first tubular member 71 adapted to comply with the bending requirements of the bending section 5 of the endoscope 1 is provided. The first tubular member 71 passes through the bending section and thus provides an exit port 96 of the working channel at the tip 4 thereof. Via a short joint tube 74, a second tubular member 73 is joined at one end with the first tubular member 71 and provides a longer intermediate section of the working channel. The second tubular member 73 is generally more rigid than the first tubular member 71. At the other end of the second tubular member 73, the second tubular member 73 is joined to a first branch of a preferably T-shaped bifurcated section 75. The bifurcated section has a second branch, which provides the entry port to the working channel together with a 75 in connection with a connector 76 or lead-in mounted on the chassis 12. In the preferred embodiment shown the bifurcated section is 75 T-shaped. That is to say perpendicular that the second branch is perpendicular to the first branch. In one embodiment, the second branch is arranged a different angle, so as to provide more of a Y-shape. The connector 76 allows a suction means to be attached for extracting fluid from a body cavity via the working channel. Alternatively a fluid source is attached to the connector 76, allowing e.g. irrigation of aspiration of the body cavity via the working channel. In one embodiment, the third branch of the bifurcated section 75 is preferably aligned with the first branch so as to provide an unobstructed straight passage through the bifurcated section 75 for the first and second motion transfer members 53, 54. A first end of a third tubular member 71 is attached to the third branch of the bifurcated section, which at least in the released position of the operating member 22 is aligned with the first and third branch of the bifurcated section 75, and the second tubular member 73, when the latter is in a relaxed position, i.e. not influenced by external forces from body cavity walls or the like. The second end of the third tubular member 71 forms the proximal end of the working channel, and is terminated in an end sealing means 51. As described above, end sealing means not only seals the proximal end of the working channel, but also serves as part a first kinematic chain by being pivotally connected to the first lever 48. The third tubular member 71 is preferably in the form of a hose of a highly flexible material, as compared to the remainder of the tubular members forming the working channel. The hose could be provided with corrugations or the like to from a bellows. Making the third tubular member of a highly flexible material serves two purposes.

The first purpose is that it allows the length of the working channel to adapt to the movement of the members of the first kinematic chain in particular the first lever 48, the first motion transfer member 53 and the interposed end sealing member 51. The flexible material allows the working channel to deform in order to adapt in length to accommodate the movement of the first motion transfer member. However, by being flexible the material also allows working channel to deform in order to comply with the swinging movement of the end sealing member caused by the first lever 48 moving the end sealing member 51 out of alignment with the first and third branches of the bifurcated member 75 and second tubular member 73. By being able to comply with these movements, the third tubular member 71 allows transfer of movement using parts of the working cannel itself, in turn, allowing transfer of movement from the operating means 22 to the tool 55 without breaching the integrity of working channel wall. Undesired ingress of pollutants is thus avoided.

The second purpose is similar to the first purpose, because by being flexible the material also allows working channel to deform in order to comply with the movement of the members of the second kinematic chain, in particular the movement of the first tubular end member 52 caused by the second lever 49 in conjunction with the arm first 50. As mentioned above this movement is transferred via the working channel wall, because the third tubular member 72 is clamped between the first tubular end member 52 and clamping member 79. By being able to comply with these movements, the third tubular member 71 allows transfer of movement using parts of the working cannel itself, in turn, allowing transfer of movement from the operating means 22 to the tool 55 without breaching the integrity of working channel wall. Undesired ingress of pollutants is thus avoided. Efficient clamping of the third tubular member 72 between the clamping member 79 and first tubular end member 52 is provided by the embodiments of the present disclosure. One issue is to ensure good grip, so that the relative position between the clamping member 79 and the first tubular end member 52 does not change due to the forces in the kinematic chain when the tool 55 is operated. The first tubular end member 52 the first tubular end member may comprise concentric ribs 98 or corrugations, or similar means. Another issue solved by the present disclosure is that in some cases a working channel with a sealed appendix at the proximal end, the output port at the distal end, and entry port located between them, it may be difficult to sterilize the interior of the appendix, in particular the proximal end thereof between the end sealing means 51 and the first tubular end member 52, because the access of sterilizing fluid, such as Ethylene Oxide, may be blocked by the first tubular end member 52. Sterilisation with Ethylene Oxide (ETO sterilization) is preferred for sterilisation.

Accordingly, as can be seen in FIG. 15A an elongate groove along the first tubular end member 52 and across the concentric ribs 98 is provided. In assembly this groove is made to register with gap in the clamping means 79, so as to allow an open fluid passage along the first tubular end member 52. Preferably, the inner diameter of the third tubular member 71 is selected to be larger than the largest outer diameter of the first tubular end member 52 so as to form a pouch in the first tubular member 71 also registering with the groove 99.

The present disclosure also solves an issue of using the working channel wall as a part of the kinematic chains, and therefore in the second kinematic chain gripping and the third tubular member 71 somewhere between the sealing end member 51 and the bifurcated section 75, may cause inadvertent overstretching of the flexible material of the third tubular member, leading, in turn, to an undesired rupture of the working channel wall. To overcome this, a strike plate 59 is provided in the chassis 12. When the clamping member 79 is moved under the by depression of the operating member 22 by the operator, the clamping member will strike the underside (as understood with reference to FIG. 1) of the strike plate 59, and will be limited in further motion. Thus even if the operator presses inappropriately hard on the operating member 22, the clamping means will not tear the third tubular member 71 and breach the integrity of the working channel wall. Preferably, the strike plate serves the dual purpose of also accommodating electronics of the endoscope 1 such as a printed circuit board 62.

In one embodiment, the tool 55 is provided as a grasping tool 120. FIG. 16 is an enlarged side view of one embodiment of a grasping head 138 of the tool 120 (subsequently also referred to as "tool 120"). A first jaw 140 includes a connecting portion 144, an intermediate portion 146 and a gripping portion 148. Similarly, a second jaw 142 includes a connecting portion 150, an intermediate portion 152 and a gripping portion 154. The jaws 140, 142 of the grasping head 138 are connected to each other at the connecting portion 144, 150. In one embodiment, the connecting portions 144, 150 are welded together.

FIG. 17 is a side view of one embodiment of the grasping head 138 in a situation where the grasping head is not finalized, i.e. it has not undergone all steps of manufacture to arrive the configuration shown in FIG. 16. In one embodiment, the grasping head 138 is manufactured from a single blank being shaped into the final shape of the grasping head 138 shown in FIG. 16 having a first thickness T1 of the connecting portion 144, 150, a second thickness T2 of the intermediate portion 146, 152, and a third thickness T3 of the gripping portion 148, 154. In one embodiment, the single blank is made from a suitable metal strip. One suitable process for manufacturing the grasping head 138 is progressive stamping which include (but is not limited to) partial processes such as punching, coining and bending. In one example, a feeding system pushes a strip of metal through stations of a progressive stamping die, wherein the individual stations performs one or more operations on the strip. Ultimately, the finished part, such as a grasping head, is separated from the carrying web of metal. In embodiments, suitable materials for the jaws 140, 142 of the grasping head 138 include stainless steel such as, but not limited to, the types AISI 304, AISI 316, 17-7 PH AISI 631.

In FIG. 17, the first jaw 140 corresponds to the left side of a centerline CL of the grasping head 138 and the second jaw 142 corresponds to the right side of the centerline CL. In one embodiment, the second thickness T2 is less (or smaller) than the third thickness T3. Providing the intermediate portion 146, 152 of a jaw 140, 142 with a lesser thickness T2 than the thickness T3 provides a grasping head 138 that requires less initial force to shift from the open state to the closed state. In one embodiment, the thickness T1 of the connecting portion 144, 150 is substantially identical to the third thickness T3 of the gripping portion 148, 154. By the term "substantially identical" is meant that the thicknesses T1 and T3 do not vary from each other by other than normal manufacturing tolerances. The reduced thickness T2 of the intermediate portion 146, 152 furthermore helps provide flexibility of the grasping head 138 in a location where it is particularly advantageous, thereby reducing the force needed to retract the grasping head 148 into the tubular member in the form of sheath 124. In turn, the larger thickness T3 of the gripping portion 148, 154 provides more stiffness where advantageous to help provide a firmer grip of the jaws 140, 142 of the grasping head 138 on a stent to be removed.

In one embodiment, the second thickness T2 of the intermediate portion 146, 152 is manufactured to be between ⅓ (one third) and ⅔ (two thirds) of the third thickness T3 of the gripping portion 148, 154.

Figure 18:
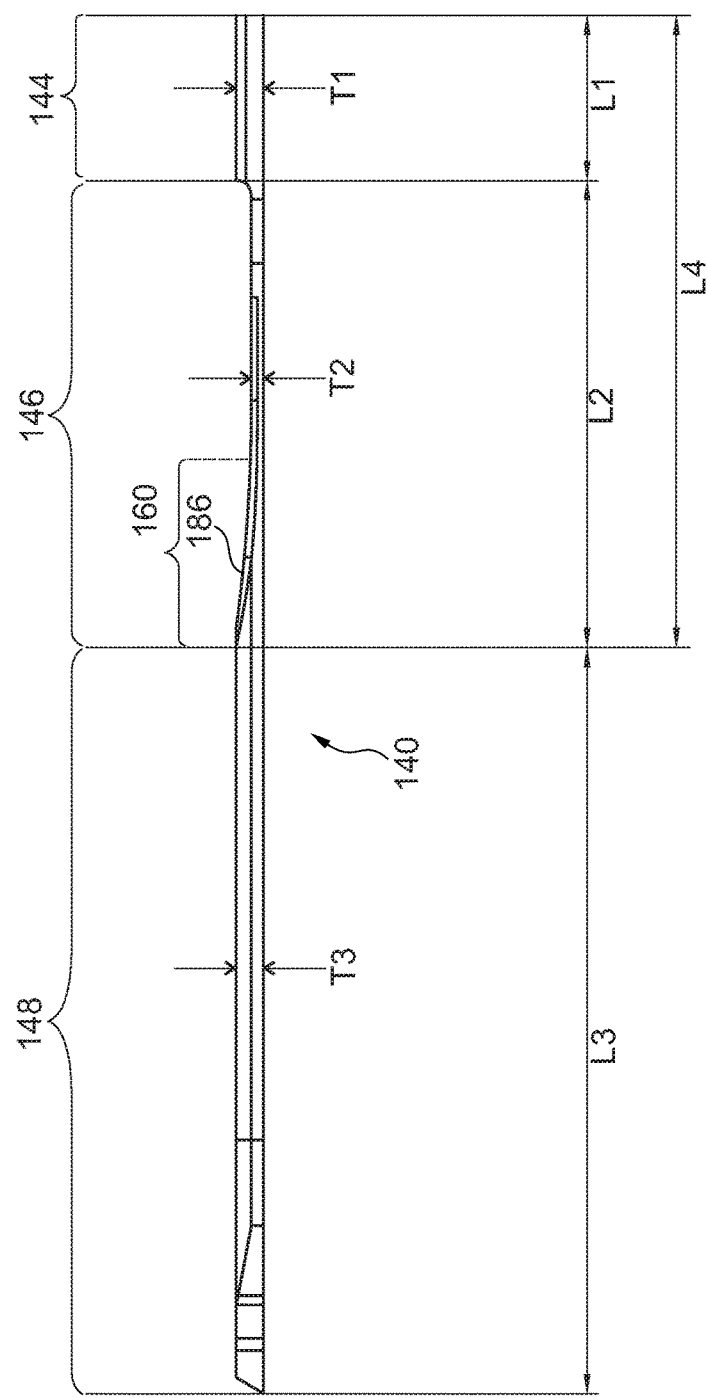
FIG. 18 is an enlarged side view of one embodiment of a first jaw of the grasping head.

FIG. 18 is an enlarged side view of one embodiment of the first jaw 140 of the grasping head 138, corresponding to an enlarged view of the left hand side of FIG. 17. In one embodiment, the intermediate portion 146 comprises a tapering zone 160 in which the thickness of the first jaw 140 transitions from the second thickness T2 of the intermediate portion 146 to the third thickness T3 of the gripping portion 148. Although FIG. 18 focuses only on the first jaw 140, it is to be understood that in embodiments the second jaw 142 likewise includes a tapering zone 160. One advantageous effect of the transition zone 160 is that, along with the lesser thickness T2 of the intermediate section 146, 152, it further reduces the force needed to shift the grasping tool 120 from the open state to the closed state during initial closing of the jaws. That is, when the grasping head 138 is retracted by actuating the tool operating member, the transition zone 160 effectively functions as a ramp for the sliding engagement between the respective jaw 140, 142 and the sheath 124. It further provides for the initial portion of the retraction sequence to be smooth, i.e. without any sudden jerks or staggered movements.

In one embodiment, a third length L3 of the gripping portion 148 exceeds a total combined length L4 of a first length L1 of the connecting portion 144 and a second length L2 of the intermediate portion 146 measured in a longitudinal direction of the grasping head 138. In one embodiment, the third length L3 of the gripping portion 148 is configured to be 4-6 times the first length L1 of the connecting portion 144 and the second length L2 of the intermediate portion 146 is configured to be 2-4 times the first length L1 of the connecting portion 144.

FIG. 19 is a top view of one embodiment of the grasping head 138 of FIG. 17 and, as in FIG. 17, shown in the not yet finalized shape of the grasping head. FIG. 19 shows the connection portion 144, 150, the intermediate portion 146, 152 and the gripping portion 148, 154 of each of the first and second jaws 140, 142. FIG. 19 further illustrates a relative widthwise extent of the connection, intermediate and gripping portions in embodiments of the grasping head 138. In one embodiment, respective connecting portions 144, 150 have a first width W1, respective intermediate portions 146, 152 have a second width W2 and respective gripping portions 148, 154 have a third width W3. In embodiments, a proximal segment 153*a* of the intermediate portion 146, 152 has a width that is less than the width W2 of a distal segment 153*b* of the intermediate portion 146, 152.

In one embodiment, the gripping portion 148 of the first jaw 140 is configured to have a plurality of (i.e. two or more) prongs 151*a*, 151*b* and the gripping portion 154 of the second jaw 142 is configured to have at least one prong 157. In embodiments, the gripping portion 154 of the second jaw 142 is configured to have one prong less than the number of prongs provided on the gripping portion 148 of the first jaw 140. In embodiments, the plurality of prongs 151*a*, 151*b* of the first jaw 140 are provided on a first end segment 149 of the gripping portion 148 of the first jaw 140, and a prong 157 of the second jaw 142 is provided on a second end segment 155 of the second jaw 142.

In one embodiment, a width W4 of the first jaw 140 at the first end segment 149 of the gripping portion 148 is greater than the width W3. In one embodiment, a width W5 of the second jaw 142 at the second end segment 155 of the gripping portion 154 is greater than the width W3. In one embodiment, the width W4 is greater than the width W5. The widths of the first and second end segments 149, 155 can be varied, such as, but not exclusively, to accommodate a specific desired number of prongs.

FIG. 19A is a cross section taken along the line A-A indicated in FIG. 19 showing a cross-section of the gripping portion 148 of one embodiment. FIG. 19A also indicates the width W3 and the thickness T3 of the gripping portion 148 at line A-A of FIG. 19. In one embodiment, edges 156, 158 of the first jaw 140 and the second jaw 142 are rounded during manufacturing so as to be smooth.

Figure 20:
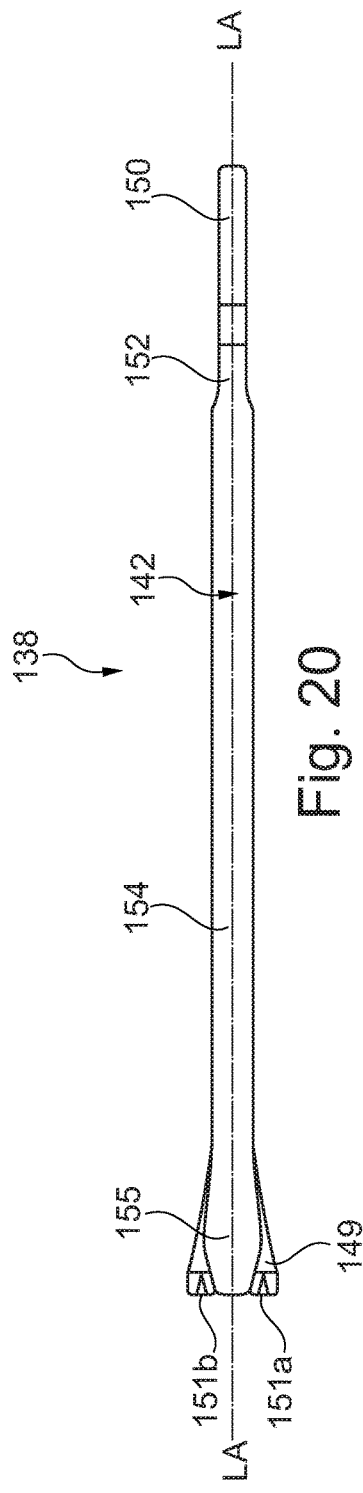
FIG. 20 is a top view of one embodiment of the grasping head of FIG. 16.

FIG. 20 is a top view of one embodiment of the grasping head 138, corresponding to the final shape shown in FIG. 16, including the blank being folded at the connecting portions 144, 150 along the centerline CL (indicated in FIG. 19). In the view of FIG. 20, the second jaw 142 is located "on top" of the first jaw 140, the first jaw therefore not being visible in the view of FIG. 20, except for some of the end segment 149 including the prongs 151, 151b. It is to be understood that in the view of FIG. 20, the prongs 151a, 151b and 157 have been shaped into the configuration indicated in FIG. 16 wherein they are generally perpendicular to a longitudinal LA axis extending through the connecting portion 144, 150. In the view of FIG. 20, the prong 157 of the second jaw 142 is to be understood as pointing away from the observer, into the plane of the paper. In one embodiment, the at least one prong 157 of the second jaw 142 is configured to fit between two neighboring prongs 151a, 151b of the first jaw 140 in the closed state. In one embodiment, the prongs 151a, 151b and 157 of the first and second jaws 140, 142 are configured to engage with each other and effectively prevent a stent to be removed from disengaging from the grasping head 138 in the closed state. In embodiments, an engagement between the prongs 151a, 151b of the first jaw 140 and the prong 157 of the second jaw 142 provides friction between the first and the second jaws which friction helps provide additional holding force of the tool 120.

FIG. 21 is a side view of one embodiment of the grasping head 138 at the distal end 128 of the sheath 124 in an open state of the tool. In one embodiment, in an open state position, the grasping head 138 locates such that an entirety of the gripping portion 148, 154 and at least some 162 of the intermediate portion 146, 152 is located beyond the distal end 128 of the sheath 124. In other words, in one embodiment, when the grasping head 138 is extended from the sheath 124, a portion 162 of the intermediate portion 148, 154 of the first jaw 140 and the second jaw 142 locates outside the distal end 128 of the sheath 124, while a remaining portion 164 is located within the sheath 124. In one embodiment, one or more prongs 151a, 151b, 157 of a respective first and second jaw 140, 142 extend in a direction away from a longitudinal axis J of the gripping portion 148, 154 at an angle K, measured between a prong 151a, 151b, 157 and the longitudinal axis J, of approximately 73 degrees. Production tolerances of ±3 degrees of the angle K are acceptable.

FIG. 22 is a side view of one embodiment of the grasping head 138 located at the distal end 128 of, and generally within, the sheath 124 in the closed state. In one embodiment, a distal end 134 of a motion transfer member 130 is connected to the connecting portion 144, 150 of the grasping head. In one embodiment, a stop 166 is provided at the distal end 134 of the motion transfer member 130 and configured to stop or control the distance that the grasping head 138 is retractable into the sheath 124. The details of the stop 166 is disclosed in further detail below with respect to FIG. 23. In one embodiment, in a closed state position, the grasping head 138 locates in the sheath 124 such that an entirety of the connecting portion 144, 150, an entirety of the intermediate portion 146, 152 and at least some 168 of the gripping portion 148, 154 is located within the sheath 124. In other words, in one embodiment, when the grasping head 138 is retracted to the full extent controlled by the provision of the stop 166, a portion 170 of the gripping portion 148, 154 of the first jaw 140 and the second jaw 142 locates outside, or extends beyond, the distal end 128 of the sheath 124.

FIG. 22A is an enlarged end view of one embodiment seen from the distal direction towards the proximal direction at the distal end 128 of the sheath 124 in the closed state such as in the view of FIG. 22. In one embodiment, a first external surface 172 of the first jaw 140 and a second external surface 174 of the second jaw 142 is configured to engage with an internal surface 176 of the distal end 128 of the sheath 124 during shifting from the open state to the closed state, or vice versa. In one embodiment, each one of the first external surface 172 of the first jaw 140 and the second external surface 174 of the second jaw 142 is configured to engage with the internal surface 176 of the sheath 124 at two engagement points 178, 180 and 182, 184. In one embodiment, in the open state the first external surface 172 of the first jaw 140 and the second external surface 174 of the second jaw 142 is an external surface of the intermediate portion 146, 152 of the respective first and second jaw 140, 142 (see FIG. 16).

In one embodiment, in the open state, a first external surface 186 (see FIG. 18) of the tapering zone 160 of the intermediate portion 146 of the first jaw 140 and a second external surface 186 of the tapering zone 160 of the intermediate portion 152 of the second jaw 142 are configured to engage with an internal surface 176 of the distal end 128 of the sheath 124.

In one embodiment, the distal end 128 of the sheath 124 is configured such that engagement between the first and second external surface 186 of the tapering zone 160 of the respective first and second jaw 140, 142 and the internal surface 176 of the distal end 128 happens at two engagement points 178, 180 and 182, 184, respectively. Providing the engagement between the external surfaces 172, 174 of the jaws 140, 142 and the internal surface 176 of the sheath 124 at two engagement points, further helps reducing the force required to overcome the friction between the jaw sections and the sheath. In embodiments, locating the external surface 186 of the tapering zone 160 of the intermediate portion at two engagement points with the sheath in the open state, further helps reducing the force required to overcome static friction between the engaging parts when initiating a shifting from the open state to the closed state.

During shifting from the open state to the closed state, in one embodiment the part of the external surface 172, 174 of the jaw 140, 142 engaging with the internal surface 176 of the sheath 124 shifts (moves) from being an external surface of the intermediate portion 146, 152 to being an external surface of the gripping portion 148, 154. During shifting from the closed to the open state, the order is reversed, i.e. the location of the engagement between the external surface 172, 174 and the internal surface 176 is initially on an external surface of the gripping portion 148, 154 followed by the engagement being at an external surface of the intermediate portion 146, 152. In other embodiments, the grasping head 138 and the distal end 128 of the sheath 124 is configured to provide the engagement between the jaws 140, 142 and the internal surface 176 at an external surface 172, 174 of the gripping portion 148, 154 alone. The specific location on the external surface 172, 174 for engagement with the internal surface 176 helps control a desired gripping force of the grasping tool 138 and also helps determine what size of stent can be removed with the grasping tool 138. In embodiments, the grasping tool 138 is adapted to grip stents having a French size FR (sometimes abbreviated CH) of 4.8-9, corresponding to Ø1.6 mm-Ø3 mm.

In one embodiment, the grasping head 138 is configured to be completely retracted into the sheath 124 in the closed state. In the closed state of this embodiment, an engagement between an external surface 172, 174 of the jaws 140, 142 and the internal surface 176 will be located at an external surface of the first end segment 149 (FIG. 19) of the gripping portion 148, 154. This is advantageous in that it helps provide a grasping tool that can be advanced and retracted to and from a working position in a body cavity or canal of a patient in a more expedient manner and simultaneously avoiding contact with tissue not relevant to the procedure during movement of the tool.

Figure 23:
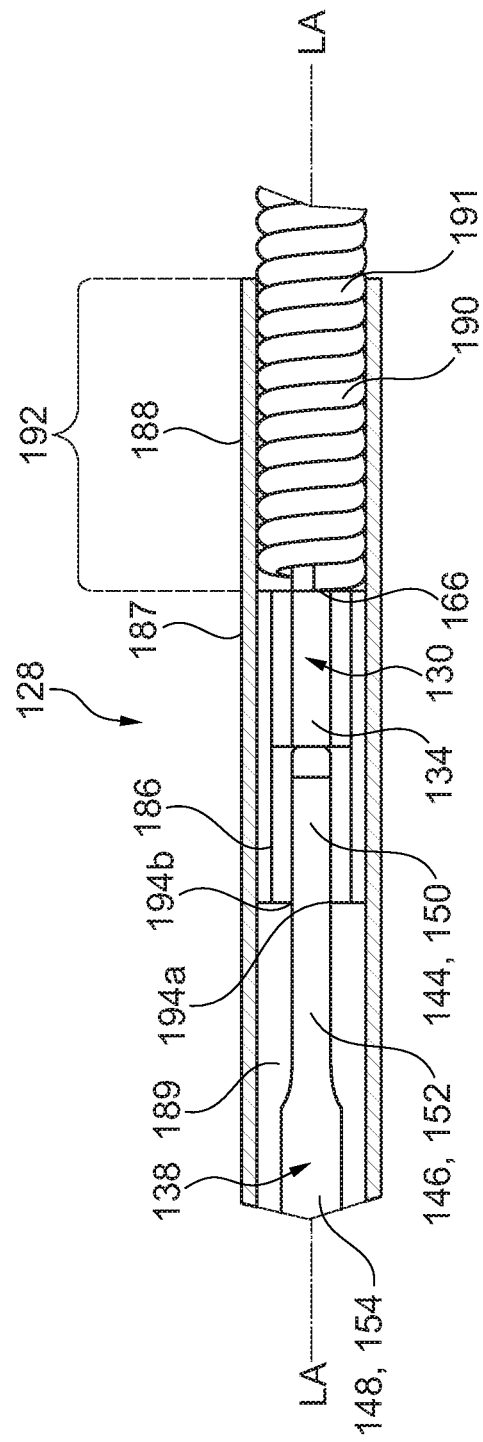
FIG. 23 is a side view of one embodiment of a distal end of a sheath of the grasping tool.

FIG. 23 is a cross-sectional view of one embodiment of the distal end 128 of the sheath 124. FIG. 23 also illustrates details of the connection between the grasping head 138 and the second distal end 134 of the motion transfer member 130. In one embodiment, a distal portion of a connecting tube 186 is welded to the connecting portion 144, 150 of the first and second jaws of the grasping head and a proximal portion of the connecting tube 186 is welded to the distal end 134 of the motion transfer member 130. In one embodiment, an outer diameter of the connecting tube 186 is configured to allow the connecting tube 186 to move linearly along longitudinal axis LA within the distal end 128 of the sheath 124, i.e. the outer diameter of the connecting tube 186 is slightly less than an inner diameter of the sheath 124. The distal end 128 of the sheath 124 defines a space 189 for the linear movement of the connected grasping head 138 and the connecting tube 186. In one embodiment, the sheath 124 includes a grasper sleeve 188. In one embodiment, the grasper sleeve 188 is located at the distal end 128 of the sheath 124. In one embodiment, the grasper sleeve 188 provides less than an entirety of the sheath 124 between the first distal end 128 and the first proximal end 126 of the sheath 124. In another embodiment, the grasper sleeve 188 provides an entirety of the sheath 124 between the first distal end 128 and the first proximal end 126.

In one embodiment, which will be explained further with respect to FIG. 24, the sheath 124 includes a plurality of components configured to provide an entirety of the sheath 124 between the first proximal end 126 and the first distal end 128. Referring to FIG. 23, in one embodiment, the outer diameter of the connecting tube 186 is greater than an inner diameter of a sheath component 190 such that a proximal portion 187 of the connecting tube 186 provides a stop 166 at a distal end of the sheath component 190. In one embodiment, the component 190 of the sheath 124 includes a round coil 191 within which the motion transfer member 130 can move. The stop 166 controls the degree to which the grasping head can be retracted into the grasper sleeve 188 when the motion transfer member 130 is moved in the proximal direction. In one embodiment, the grasper sleeve 188 is welded to the round coil 191 along an overlap 192 between them. In one embodiment, the connecting portion 144, 150 is welded to the connecting tube 186 at 194a, 194b to close off the distal portion of the connecting tube 186.

Figure 24:
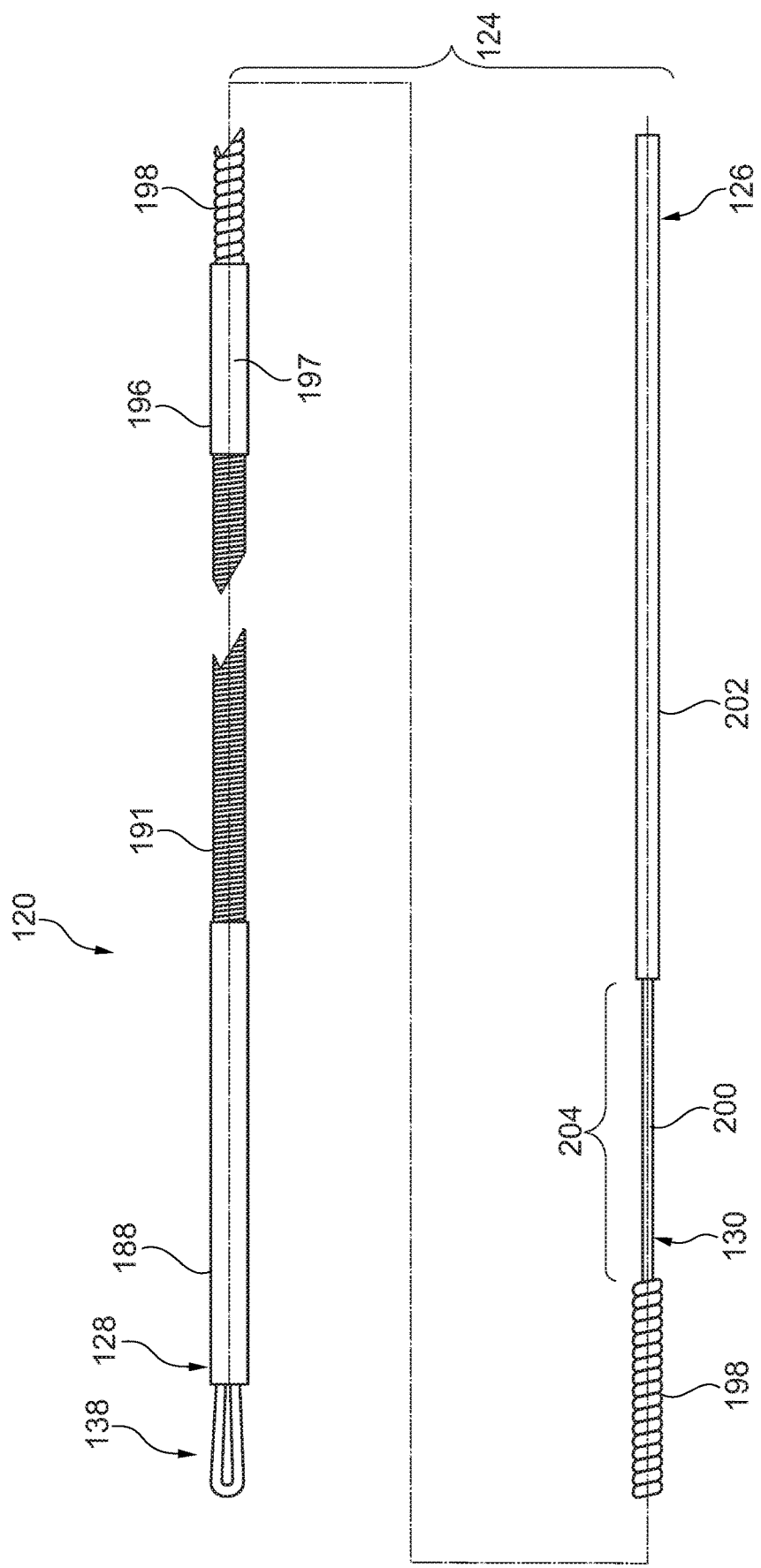
FIG. 24 is an enlarged side view illustrating a sheath, a motion transfer member and a grasping head of one embodiment of the grasping tool.

FIG. 24 is an enlarged side view illustrating a sheath 124, a motion transfer member 130 and a grasping head 138 of one embodiment of the grasping tool 120. In one embodiment, a plurality of components of the sheath 124 includes a grasper sleeve 188, a round coil 191, a flat coil 198, a coil sleeve 196 and an end sleeve 202. In one embodiment, the coil sleeve 196 is provided around the coils 196, 198 at a transition 197 between the coils. The coil sleeve 196 connects the round coil 191 and the flat coil 198. In one embodiment, the coil sleeve 196 is welded to the round coil 191 and to the flat coil 198. In one embodiment, a proximal end of the grasper sleeve 188 is welded to the round coil 191. In one embodiment, the end sleeve 202 is configured to be located at the first proximal end 126 of the sheath 124 and extends distally at least a partway towards engagement with another one of the plurality of components 188, 191, 196, 198 of the sheath 124.

In one embodiment, the flat coil 198 is provided distal to the end sleeve 202, and the round coil 191 is provided distal to the flat coil 196, with the coil sleeve 196 connecting the two coils 191, 198, and the grasper sleeve 188 connected to and extending from a distal end of the round coil 191. By virtue of their cross-sectional profiles, the flat coil component 198 provides for a stiffer or more rigid section of the sheath 124 and the round coil 191 provides for a more pliable, less rigid section of the sheath 124. Configuring the round, more flexible coil 191 distal to the flat, more rigid coil 198 of the sheath 124 helps provide optimized handling of the tool 120 such as during insertion into a body canal or cavity. In embodiments, the different components of the sheath are configured to have different individual bending and tension properties. In embodiments, the individual components are configured to have different individual inner diameters. In embodiments, individual lengths of the components 188, 191, 196, 198, 202 making up the sheath 124 are selected to meet different specifications (such as but not limited to more or less flexibility) dependent on the particular use of the grasping tool 120.

In one embodiment, the motion transfer member 130 is an inner wire 200 linearly movable within the plurality of components 188, 191, 196, 198, 202 making up the sheath 124. In one embodiment, the flat coil 198 and the end sleeve 202 do not engage, thereby providing an open zone 204 along the sheath 124 making the inner wire 200 accessible. In one embodiment, a proximal end of the inner wire 200 is connected to the tool-operating member 136.

Figure 25:
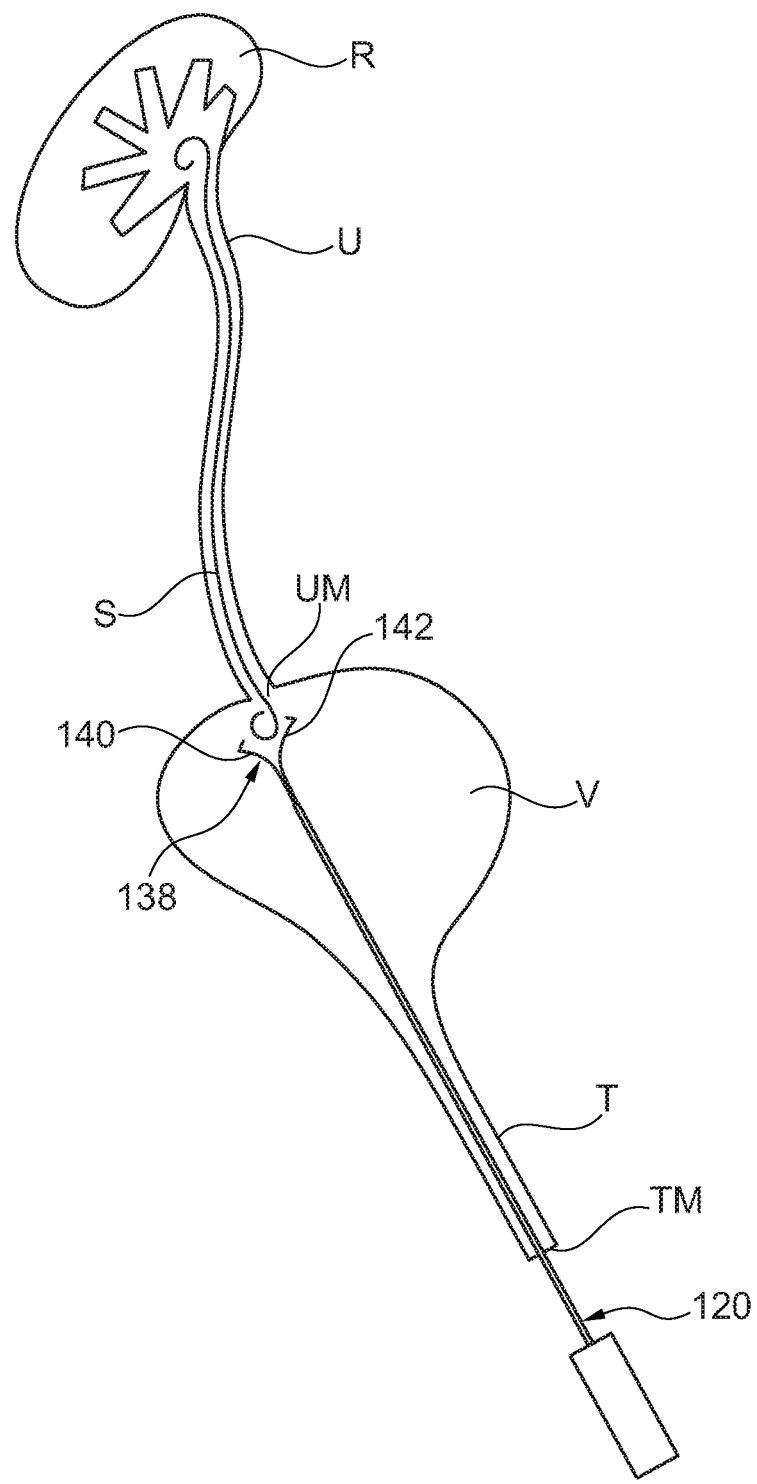
FIGS. 25 and 26 are schematic views illustrating use of the grasping tool to remove a stent from a body cavity of a patient.
Figure 26:
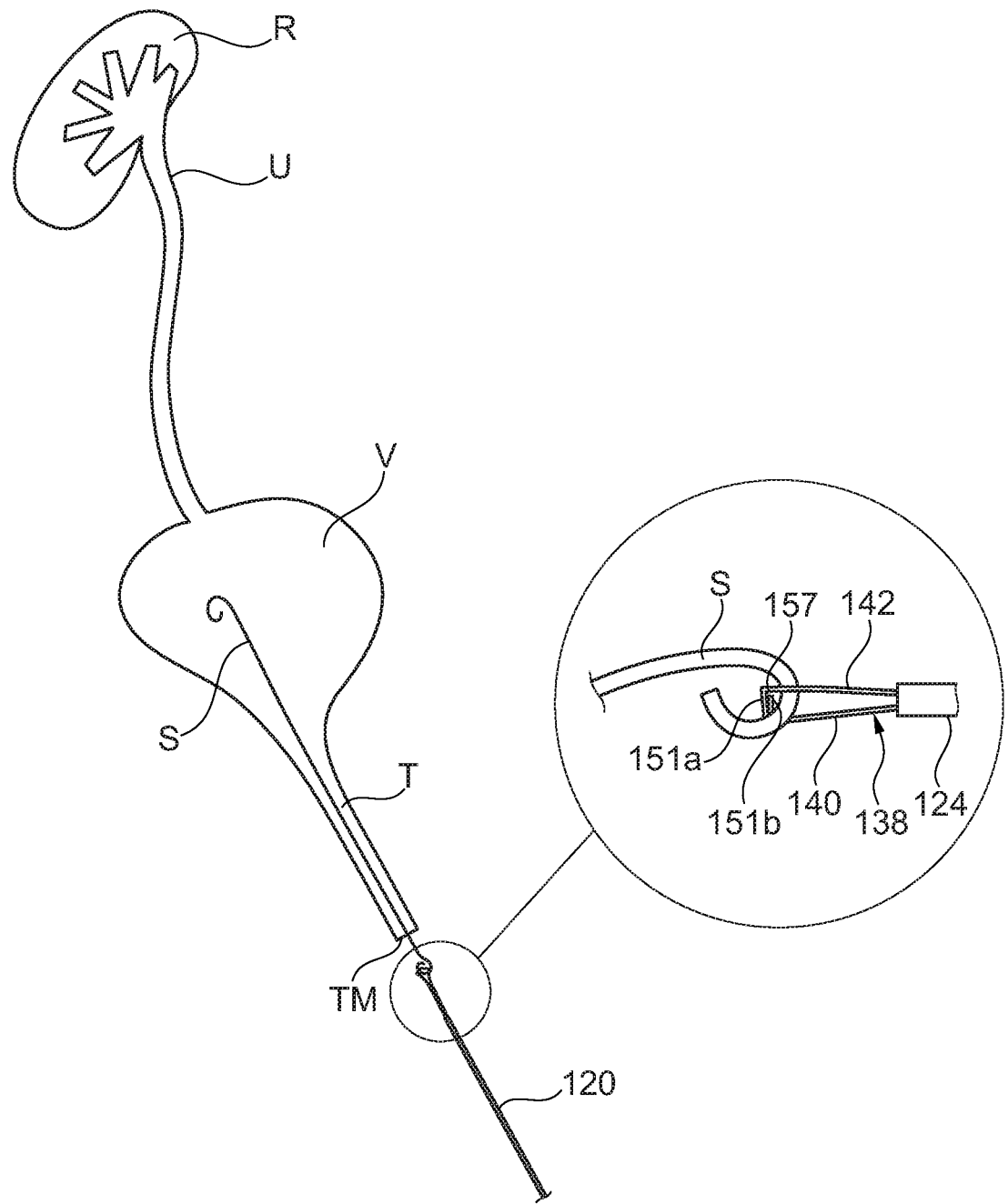

FIGS. 25 and 26 are schematic views illustrating a use of the grasping tool 120 to remove a stent from a body cavity of a patient. In the illustrated exemplary use of the tool 120 in FIGS. 25 and 26, the tool 120 is used for removal of a ureteral stent S, such as, but not limited to, a JJ- or pigtail-stent, located in a ureter U of the patient between the kidney R and the bladder V. In the illustrated example, one of the "pigtails" of the stent S is located in the bladder V just outside of a ureteral meatus UM. In the example, the grasping tool 120 is first inserted at the urethral meatus TM and advanced through the urethra T into the patient's bladder V. The grasping tool 120 further operates to extend the grasping head 138 from the distal end of the sheath and to open the jaws 140, 142 and position them around a suitable gripping location on the stent S. The grasping tool 120 then operates to firmly close the jaws 140, 142 around the stent S. The grasping tool 120 now engaged with the stent S is retracted via the bladder V and the urethra T such that the stent S is removed. FIG. 26 illustrates a situation in which the grasping tool 120 itself has been retracted to a position just outside the urethral meatus TM while a majority of the stent S has not left the urinary tract of the patient. An enlarged detail in FIG. 26 illustrates the gripping of the stent S by the jaws 140, 142 of the grasping head 138. The stent S is maintained in a firm hold by the grasping head 138 when the tool 120 is in the closed state. The prongs 151a, 151b of the first jaw 140 and the prong 157 of the second jaw engage to assist in keeping the stent S firmly secured from escaping the grip of the jaws 140, 142.

In one advantageous implementation, the grasping tool 120 is extendable from the endoscope 1 that is inserted into the bladder V through the urethra T and used for locating a suitable gripping location on the stent S.

In one aspect, the present disclosure relates to a method of removing a stent from a patient.

Figure 27:
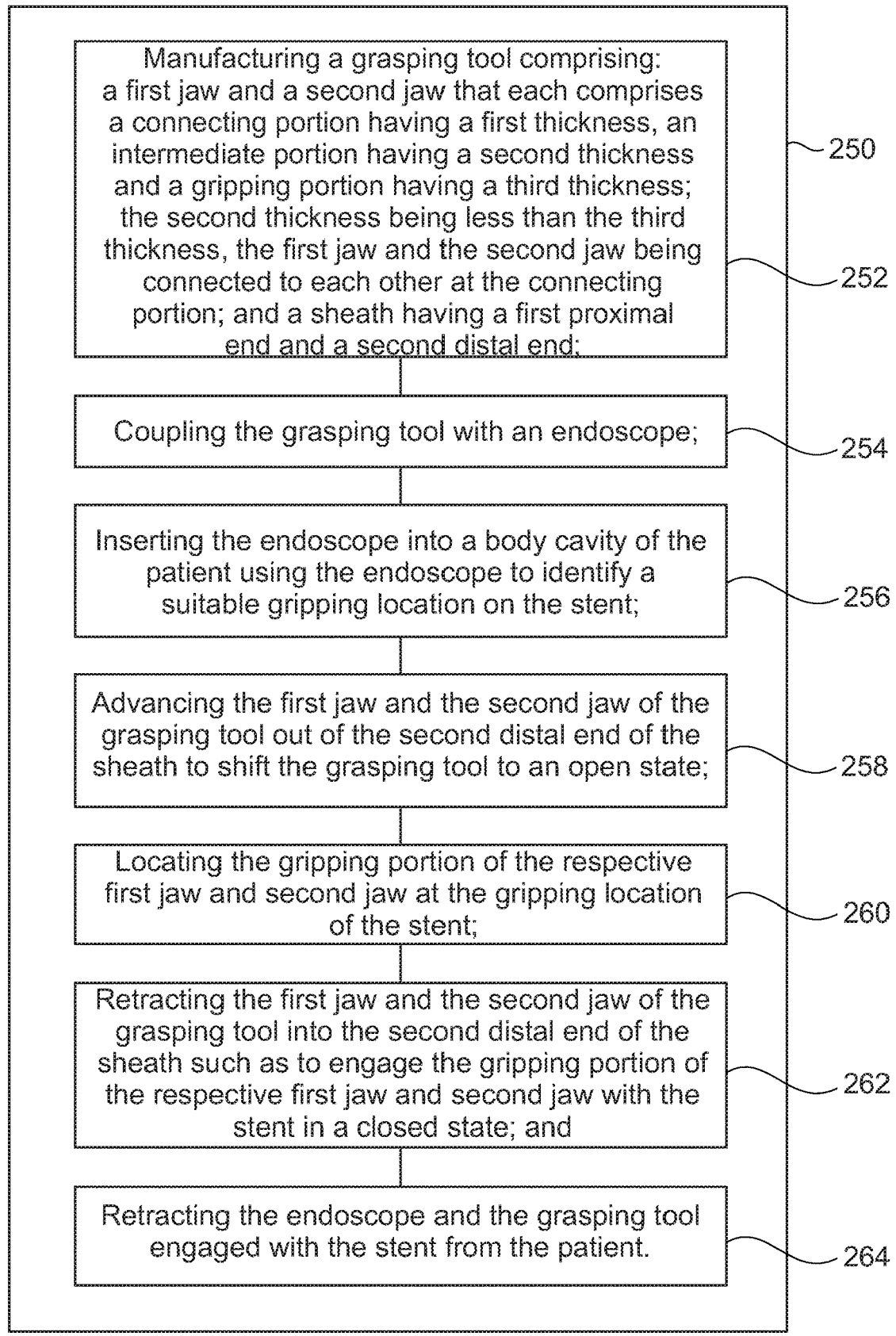
FIG. 27 is a box diagram illustrating one embodiment of a method of removing a stent from a patient.

FIG. 27 is a box diagram view illustrating one embodiment of a method 250 of removing a stent from a patient at 252 including manufacturing a grasping tool 120. The grasping tool includes a first jaw 140 and a second jaw 142. Each jaw 140, 142 comprises a connecting portion 144, 150 having a first thickness, an intermediate portion 146, 152 having a second thickness and a gripping portion 148, 154 having a third thickness. The second thickness T2 is less (or smaller) than the third thickness T3. The first jaw 140 and the second jaw 142 are connected to each other at the connecting portion 144, 150. The grasping tool 120 also includes a sheath 124 having a first proximal end 126 and a second distal end 128.

At 254, the method includes coupling the grasping tool 120 with an endoscope. In embodiments, the grasping tool 120 is configured to move within an insertion tube of the endoscope. The grasping tool 120 can be advanced, retracted and actuated (the jaws can be opened and closed) via controls on a handle of the endoscope. In one embodiment, the coupling of the endoscope and the grasping tool 120 is carried out a manufacture so as to offer a combined instrument to users. In another embodiment, the endoscope and the grasping tool are offered separately to users, whereby the coupling of the endoscope and the grasping tool is carried out by the health care professional in preparation for the procedure for removal of the stent.

At 256, the method includes inserting the endoscope coupled with the grasping tool 120 into a body cavity of the patient using the endoscope to identify a suitable gripping location on the stent. In one embodiment, the method includes inserting the endoscope via a urethra into a bladder or a ureter of the patient. At 258, the method includes advancing the first jaw 140 and the second jaw 142 of the grasping tool 120 out of the second distal end 128 of the sheath 124 to shift the grasping tool 120 to an open state. No longer confined by the sheath 124, the jaws 140, 142 are configured to move away from each other and open up. At 260, the method includes locating the gripping portion 148, 154 of the respective first and second jaw 140, 142 at the gripping location of the stent.

At 262, the method includes retracting the first jaw 140 and the second jaw 142 of the grasping tool 120 into the second distal end 128 of the sheath 124 such as to engage the gripping portion 148, 154 of the respective first jaw 140 and second jaw 142 with the stent in a closed state.

At 264, the method includes retracting the endoscope and the grasping tool engaged with the stent from the patient. In one embodiment, the method includes removing a ureteral stent by retracting the endoscope and grasping tool engaged with the ureteral stent out via the patient's urethra.

Figure 28:
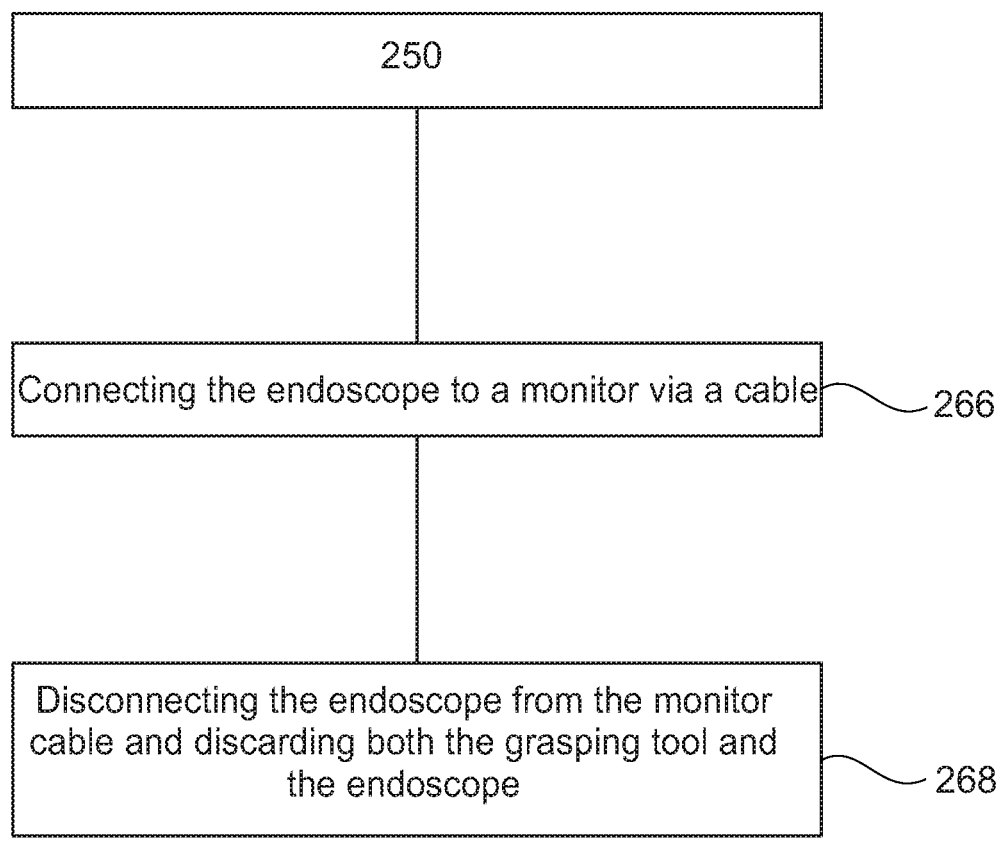
FIG. 28 is a box diagram illustrating embodiments of a method of removing a stent from a patient.

FIG. 28 is a box diagram view illustrating further embodiments of the method of removing a stent from a patient. In one embodiment, at 266, the method includes connecting the separate handle housing to a monitor via a cable. In one embodiment, at 268, the method includes disconnecting the endoscope from the separate handle housing and discarding both the grasping tool 120 and the endoscope. In one embodiment, the endoscope and the grasping tool are discarded in a container for bio-hazardous materials.

In one aspect, the present disclosure relates to a kit of parts including an endoscope, a grasping tool and a set of instructions for use. In one embodiment, the set of instructions for use provide a method for removing a stent from a patient.

The present disclosure provides an endoscope with a working channel, used not only for accommodating parts of the control mechanism of a tool but also forming itself a part of the control mechanism. The skilled person will understand that the arrangements described above, and in particular, the kinematic chains are only exemplary embodiments, and that the endoscope can be devised in many different variants without departing from the scope of the appended claims.

The endoscope and grasping tool presented in this disclosure is configured to obtain sufficient holding force of the grasping tool jaws to close around and secure a stent while requiring reduced operating force to shift the tool from the open state to the closed state. Reducing the necessary force to shift the tool from the open state to the closed state, while maintaining sufficient holding force, allows for the tool and endoscope components, particularly force transferring or moving components, to be of reduced dimensions and/or made from lightweight (less bulky) materials. This is turn allows the grasping tool and the endoscope to be of relatively low-cost, thus providing for single-use of these. This is particularly advantageous in that it provides for a much more efficient and cost-reduced surgical procedure by eliminating the need for repeated sterilizations of the endoscope and the tool (as single-use products, the endoscope and the grasping tool are one-time sterilized at manufacture before being supplied to users). Providing a single-use endoscope and tool also helps reduce risk of cross-contamination between patients and reduce bottlenecks in equipment availability.

As the endoscope and tool allows single handed use of the endoscope, methods of operation can be obtained in which a single health care professional can operate the endoscope and tool, thereby reducing the number of staff required to carry out a procedure, in turn providing easier access to the procedure and reduce the costs involved.

The invention claimed is:

1. A method of removing a stent from a patient, the method comprising:
    providing a grasping tool comprising:
        a first jaw having a first connecting portion and a second jaw having a second connecting portion, with the first connecting portion and the second connecting portion connected together by a fold and combining to define a proximal end of the grasping tool, with the proximal end of the grasping tool having a first thickness, each of the first jaw and the second jaw comprising an intermediate portion having a second thickness and a gripping portion located at a distal end of the grasping tool and having a third thickness; where the intermediate portion is located to extend between the first connecting portion and the second connecting portion at the proximal end of the grasping tool and the gripping portion at the distal end of the grasping tool, with the second thickness being less than the first thickness and less than the third thickness; and a sheath disposed around the grasping tool, with the sheath having a first proximal end and a second distal end;

coupling the grasping tool to an endoscope;

inserting the endoscope through a urethra and into a bladder of the patient;

identifying a gripping location on the stent with the endoscope;

deploying the grasping tool to an open state by advancing the first jaw and the second jaw of the grasping tool out of the second distal end of the sheath;

locating the gripping portion of the respective first jaw and second jaw at the gripping location of the stent;

sliding an external surface of the first jaw and the second jaw of the grasping tool against an internal surface of the second distal end of the sheath by retracting the first jaw and the second jaw of the grasping tool into the second distal end of the sheath and closing the gripping portion of the respective first jaw and the second jaw onto the gripping location on the stent; and retracting the endoscope, the grasping tool, and the stent from the bladder and the urethra of the patient.

2. A method according to claim 1, further comprising connecting the endoscope to a monitor via a cable.

3. A method according to claim 2, wherein the endoscope is a camera endoscope, the method further comprising:

disconnecting the camera endoscope from the cable and discarding both the grasping tool and the camera endoscope.

4. A method according to claim 1, wherein sliding the external surface of the first jaw and the second jaw of the grasping tool against the internal surface of the second distal end of the sheath comprises manipulating a tool operating member on the endoscope.

5. The method of claim 1, comprising identifying a tail of the stent located inside of the bladder and outside of a ureteral meatus with the endoscope; and closing the gripping portion of the respective first jaw and the second jaw onto the tail of the stent.

6. The method of claim 1, comprising locating the gripping portion of the respective first jaw and second jaw inside of the bladder and outside of a ureteral meatus; identifying a portion of the stent extending out of the ureteral meatus and exposed inside of the bladder; and closing the gripping portion of the respective first jaw and the second jaw onto the portion of the stent extending out of the ureteral meatus.

7. The method of claim 1, wherein the endoscope is a single-use camera endoscope that is one-time sterilized at manufacture, the method further comprising:

retracting the single-use camera endoscope, the grasping tool, and the stent from the bladder and the urethra of the patient and discarding the single-use camera endoscope in a bio-hazard container.

8. A method of removing a stent from a patient, the method comprising:

providing a grasping tool having a first jaw connected to a second jaw at a proximal connecting portion, with the first jaw and the second jaw each having a distal end provided with a gripping portion and an intermediate portion connected between the proximal connecting portion and the distal end, where a thickness of the intermediate portion is less than a thickness of the proximal connecting portion and less than a thickness of the gripping portion, and a sheath disposed around the grasping tool, with the grasping tool having the first jaw folded into contact with the second jaw at the proximal connecting portion of the grasping tool;

coupling the grasping tool to a motion transfer member of a single-use camera endoscope;

inserting the single-use camera endoscope through a urethra and into a bladder of the patient;

identifying a ureteral stent inside of the patient with the single-use camera endoscope;

deploying the grasping tool from the single-use camera endoscope by advancing the first jaw and the second jaw of the grasping tool distally out of a distal end of the sheath;

retracting the grasping tool proximally into the distal end of the sheath with the motion transfer member and sliding an external surface of the first jaw and the second jaw of the grasping tool against an internal surface of the distal end of the sheath and closing distal portions of the first jaw and the second jaw about the ureteral stent;

retracting the single-use camera endoscope, the grasping tool, and the ureteral stent from the urethra of the patient; and discarding the single-use camera endoscope in a bio-hazard container.

9. The method of claim 8, further comprising:

discarding both of the single-use camera endoscope and the grasping tool in the bio-hazard container.

10. The method of claim 8, further comprising:

configuring the thickness of the intermediate portion of the first jaw and the intermediate portion of the second jaw to reduce a retraction force for moving the grasping tool proximally into the distal end of the sheath.

11. The method of claim 8, further comprising:

configuring the gripping portion of the first jaw and the gripping portion of the second jaw to have an increased stiffness relative to the intermediate portion of the first jaw and the second jaw.

12. A method of removing a stent from a patient, the method comprising:

providing a grasping tool having a first jaw folded into contact with a second jaw at a proximal connecting portion, with the first jaw and the second jaw each having a distal end provided with a gripping portion and an intermediate portion connected between the proximal connecting portion and the distal end, where a thickness of the intermediate portion is less than a thickness of the proximal connecting portion and less than a thickness of the gripping portion, and a sheath disposed around the grasping tool;

coupling the grasping tool to a camera endoscope;

coupling the camera endoscope to a video monitor;

inserting the camera endoscope through a urethra and into a bladder of the patient;

viewing, with the video monitor, a ureteral stent having a stent portion in a ureter of the patient and a tail portion extending out of a ureteral meatus and into the bladder of the patient;

deploying the grasping tool from the camera endoscope by advancing the first jaw and the second jaw of the grasping tool distally out of a distal end of the sheath;

retracting the grasping tool proximally into the distal end of the sheath and sliding an external surface of the first jaw and the second jaw of the grasping tool against an internal surface of the distal end of the sheath and closing distal portions of the first jaw and the second jaw about the tail portion of the ureteral stent; and retracting the camera endoscope, the grasping tool, and the ureteral stent from the urethra of the patient.

13. The method of claim 12, further comprising discarding the camera endoscope in a bio-hazard container.

14. The method of claim 12, further comprising:
discarding both of the camera endoscope and the grasping tool in the bio-hazard container.

15. The method of claim 12, further comprising:
configuring the thickness of the intermediate portion of the first jaw and the intermediate portion of the second jaw to reduce a retraction force for moving the grasping tool proximally into the distal end of the sheath.

16. The method of claim 12, further comprising:
configuring the gripping portion of the first jaw and the gripping portion of the second jaw to have an increased stiffness relative to the intermediate portion of the first jaw and the second jaw for providing a firmer grip for closing the distal portions of the first jaw and the second jaw about the tail portion of the ureteral stent.

* * * * *